United States Patent [19]

Blankley et al.

[11] Patent Number: 4,812,462

[45] Date of Patent: Mar. 14, 1989

[54] 4,5,6,7-TETRAHYDRO-1H-IMIDAZO[4,5-C]PYRIDINE-6-CARBOXYLIC ACID ANALOGS HAVING ANTIHYPERTENSIVE ACTIVITY

[75] Inventors: C. John Blankley; John C. Hodges; John S. Kiely; Sylvester R. Klutchko, all of Ann Arbor, Mich.

[73] Assignee: Warner-Lambert Company, Morris Plains, N.J.

[21] Appl. No.: 847,067

[22] Filed: Apr. 1, 1986

[51] Int. Cl.[4] .................... C07D 471/04; A61K 31/44
[52] U.S. Cl. ..................................... 514/303; 546/118
[58] Field of Search ................... 514/303; 546/82, 118

[56] References Cited

U.S. PATENT DOCUMENTS 4,141,899  2/1979  Arcari et al. .................. 546/118
4,223,146  9/1980  Arcari et al. .................. 546/118

FOREIGN PATENT DOCUMENTS 902611  6/1985  Belgium .................. 546/82

*Primary Examiner*—Mary C. Lee
*Assistant Examiner*—Zinna Northington
*Attorney, Agent, or Firm*—Joan Thierstein

[57] ABSTRACT

This invention relates to novel substituted derivatives of 4,5,6,7-tetrahydro-1H-imidazo[4,5-c]pyridine-6-carboxylic acid and analogs thereof, which are useful for the treatment of hypertension, as well as, novel pharmaceutical compositions and methods of use.

16 Claims, No Drawings

4,5,6,7-TETRAHYDRO-1H-IMIDAZO[4,5-C]PYRIDINE-6-CARBOXYLIC ACID ANALOGS HAVING ANTIHYPERTENSIVE ACTIVITY

BACKGROUND OF THE INVENTION

This invention relates to novel substituted derivatives of 4,5,6,7-tetrahydro-1H-imidazo[4,5-c]pyridine-6-carboxylic acid and analogs thereof which are useful for the treatment of hypertension. U.S. Pat. No. 4,141,899 to Arcari et al. issued Feb. 27, 1979, discloses 4,5,6,7-tetrahydroimidazo[4,5-c]pyridine derivatives as antiulcer and antisecretory agents. Further examples are disclosed in Arzneim. Forsch. 34 (11) 1467–1471 (1984). These compounds differ from the ones disclosed in this invention in that they lack a substituent group at the 6-position. This variation, in combination with substitution at other positions of the imidazo[4,5-c]pyridine ring provide novel compounds now found to have antihypertensive activity. Japanese Patent applications J5 9095-286A to Otsuka Seiyaku Kojy, published Jan. 6, 1984, discloses imidazo[4,5-c]pyridine 6-carboxylic acid derivatives having psycholeptic, hypotensive, central nervous system or analeptic activity.

A Belgian Patent No. 902,611 entitled "New Imidazo-Pyridine-6-Carboxamide Derivatives Useful as Antiviral Agents" discloses related compounds limited to an amide function in a C$_6$ position of a nuclear structure having the positions numbered as shown in the formula as follows:

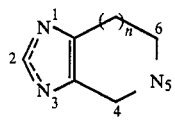

Such compounds limited to the amide function are disclosed by Belgian Patent No. 902,611 as pharmaceutically active agents. Additionally related compounds having a carboxyl function at the C$_6$ position are disclosed by the Belgian Patent No. 902,611 but only for use as intermediates.

Thus the compounds of the first three of the above references differ from those disclosed in this invention by virtue of bearing no substituent groups at N$_1$, N$_3$, N$_5$, or C$_4$; but carrying a spiro ring at C$_4$. Further the present invention excludes compounds having a carboxylic acid group disclosed only as intermediates in Belgian Patent No. 902,611 discussed above. The present invention is thus pharmaceutical compositions having compounds of formula I' as defined hereinafter and a pharmaceutically acceptable carrier and method of use therefor. Such differences provide unobvious variance over the prior art.

SUMMARY OF THE INVENTION

The present invention is a novel analog of 4,5,6,7-tetrahydroimidazo[4,5-c]pyridine having the formula (I):

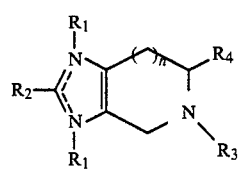

and their pharmaceutically acceptable base or acid addition salts; wherein (1) --- is a single or double bond;
(2) one of R$_1$ is present and is
 (a) alkyl of from four to twenty carbons, inclusive,
 (b)

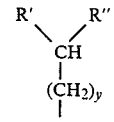

wherein y is zero, one, two, three, four or five, R' is cycloalkyl, naphthyl, heteroaryl, phenyl unsubstituted or substituted with of from one through five, preferably one through three, substituents comprising lower alkyl, halo, trifluoromethyl, hydroxy, lower alkoxy, lower acyloxy, amino, N-lower monoalkylamino, N,N-lower dialkylamino, lower thioalkyl, lower alkylsulfonyl, nitro or $$-\underset{\underset{O}{\|}}{N}HCR_{10}$$

wherein R$_{10}$ is lower alkyl, phenyl unsubstituted or substituted by lower alkyl, or —NHR$_{11}$ wherein R$_{11}$ is hydrogen or lower alkyl, and R" is hydrogen, lower alkyl, cycloalkyl, naphthyl, phenyl unsubstituted or substituted with of from one through five substituents, preferably from one through three substituents, comprising alkyl, halo, trifluoromethyl, amino, N-lower monoalkylamino, N,N-lower dialkylamino, lower thioalkyl, lower alkylsulfonyl, or nitro;
(3) R$_2$ is
 (a) hydrogen,
 (b) halo,
 (c) lower alkyl,
 (d) R'$\pm$CH$_2\pm_x$ wherein x is one, two, three, four, or five and R' is independently as defined above,
 (e)

wherein R' is independently as defined above, or
(f) R'—CH(OH)— wherein R' is independently as defined above;
(4) R$_3$ is
 (a) R'$\pm$CH$_2\pm_x$ wherein x and R' are independently as defined above,
 (b)

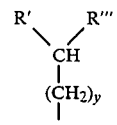

wherein R' and y are independently as defined above, and R''' is lower alkyl, cycloalkyl, naphthyl, phenyl unsubstituted or substituted with of from one through five substituents, preferably from one through three substituents, comprising alkyl, halo, trifluoromethyl, amino, N-lower monoalkylamino, N,N-lower dialkylamino, lower thioalkyl, lower alkylsulfonyl, or nitro;

(c)

wherein $R_5$ is (i) alkyl of from one to fifteen carbons, inclusive, (ii)

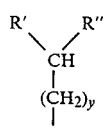

wherein R', R'' and y are independently as defined above, (iv) $-(CH=CR_6)-R_1$, wherein $R_6$ is hydrogen or lower alkyl and $R_1$ is as defined above, (v)

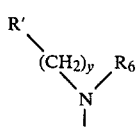

wherein y, R' and $R_6$ are independently as defined above, (vi) $R'-(CH_{2y})-$ wherein y and R' are independently defined above, (vii)

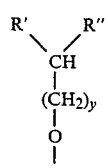

wherein R', R'', and y are independently as defined above, (d)

wherein $R_5$ is independently as defined above, preferably $R'-(CH_{2y})-$ wherein R' and y are independently as defined above;

(5) $R_4$ is (a) $-CH_2OR_7$ wherein $R_7$ is hydrogen, lower acyl, a lower alkyl, (b)

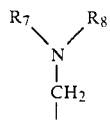

wherein $R_7$ is independently as defined above and $R_8$ is hydrogen, lower alkyl, or benzyl.

(c)

(d) $-C\equiv N$, (e)

wherein $R_9$ is hydrogen, lower alkyl or benzyl; and (6) n is zero, one, two, or three; with the overall proviso that $R_9$ cannot be hydrogen when $R_3$ is $R'-(CH_{2x})-$ or

wherein $R_5$ is $R'-(CH_{2y})-$ or

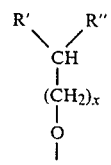

wherein each of R', R'', x and y are as defined above.

Further, the present invention is a novel compound of formula (II):

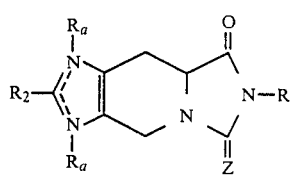

and the nontoxic, pharmaceutically acceptable base or acid addition salts thereof, wherein === is as defined above;

(1) one of $R_a$ is present and is (a) hydrogen, (b) alkyl of from one to twenty carbons, inclusive, (c)

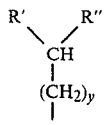

wherein y, R' and R" are independently as defined above; and (2) Z is oxygen or sulfur; and (3) $R_2$ is independently as defined above.

(4) R is lower alkyl, heteroaryl, pheny or benzyl each unsubstituted or substituted with of from one through five, preferably one through three, substituents comprising lower alkyl, halo, trifluoromethyl, hydroxy, lower alkoxy, lower acyloxy, amino, N-lower monoamino, N,N-lower dialkylamino, lower thioalkyl, lower alkylsulfonyl, or nitro.

The compounds of formula I, that are preferred, are those wherein $R_2$ is H, $R_3$ is

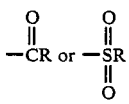

and n is one or two, or more particularly, the preferred compounds of formula I, that are preferred, have the formula (XX)

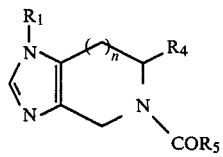

wherein $R_1$, n, $R_4$ and $R_5$ are as defined above.

More preferred are the compounds of formula XX wherein $R_1$ is

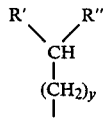

wherein R' is phenyl unsubstituted or substituted as defined above, R" is hydrogen and y is zero, one, or two, and $R_5$ is

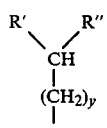

wherein R', R" and y are as defined above.

The novel compounds of formula II of the present invention are intermediates useful in the preparation of selected derivatives shown above as novel compounds having the formula I as defined above.

Additionally, the present invention has found that selected intermediates that are novel compounds of formula II as defined above also possess useful antihypertensive activity.

Thus, the preferred compounds of formula II according to the present invention are compounds that are (1) intermediates useful in the preparation of preferred compounds of formula I and (2) compounds having use as antihypertensive agents.

The compounds of formula II having antihypertensive activity are those having the formula (IIa)

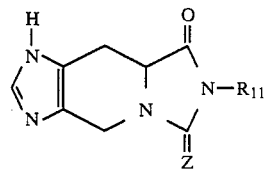

wherein Z is as defined above and $R_{11}$ is branched alkyl of from three to five carbons, inclusive, and unsubstituted and substituted phenyl as defined above, preferably phenyl substituted by one to three methoxy substituents, inclusive.

The present invention is also directed to novel processes for the preparation of the compounds of the present invention. That is, the processes for the preparation of compounds of the formula I and the processes for the preparation of compounds of the formula II are both the present invention.

Additionally, the present invention is directed to a pharmaceutical composition for treating hypertension in mammals comprising an antihypertensive effective amount of the compound of formula (I')

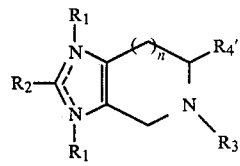

and their pharmaceutically acceptable base or acid addition salts; wherein (1) == is a single or double bond;

(2) one of $R^1$ is present and is (a) alkyl of from four to twenty carbons, inclusive, (b)

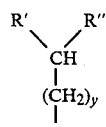

wherein y is zero, one, two, three, four or five, R' is cycloalkyl, naphthyl, heteroaryl, phenyl unsubstituted or substituted with of from one through five, preferably one through three, substituents comprising lower alkyl, halo, trifluoromethyl, hydroxy, lower alkoxy, lower acyloxy, amino, N-lower monoalkylamino, N,N-lower dialkylamino, lower thioalkyl, lower alkylsulfonyl, nitro or

wherein $R_{10}$ is lower alkyl, phenyl unsubstituted or substituted by lower alkyl, or —$NHR_{11}$ wherein $R_{11}$ is hydrogen or lower alkyl, and R″ is hydrogen, lower alkyl, cycloalkyl, naphthyl, phenyl unsubstituted or substituted with of from one through five substituents, preferably from one through three substituents, comprising alkyl, halo, trifluoromethyl, amino, N-lower monoalkylamino, N,N-lower dialkylamino, lower thioalkyl, lower alkylsulfonyl, or nitro;

(3) $R_2$ is
 (a) hydrogen,
 (b) halo,
 (c) lower alkyl,
 (d) R′—$(CH_2)_x$— wherein x is one, two, three, four, or five and R′ is independently as defined above,
 (e)

wherein R′ is independently as defined above, or
 (f) R′—CH(OH)— wherein R′ is independently as defined above;

(4) $R_3$ is
 (a) R′—$(CH_2)_x$— wherein x and R′ are independently as defined above,
 (b)

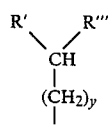

wherein R′ and y are independently as defined above, and R‴ is lower alkyl, cycloalkyl, naphthyl, phenyl unsubstituted or substituted with of from one through five substituents, preferably from one through three substituents, comprising alkyl, halo, trifluoromethyl, amino, N-lower monoalkylamino, N,N-lower dialkylamino, lower thioalkyl, lower alkylsulfonyl, or nitro;
 (c)

wherein $R_5$ is
 (i) alkyl of from one to fifteen carbons, inclusive,
 (ii)

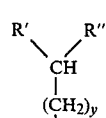

wherein R′, R″ and y are independently as defined above, (iv) —$(CH=CR_6)$—$R_1$, wherein $R_6$ is hydrogen or lower alkyl and $R_1$ is as defined above.
 (v)

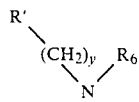

wherein y, R′ and $R_6$ are independently as defined above,
 (vi) R′—$(CH_2y)$— wherein y and R′ are independently as defined above,
 (vii)

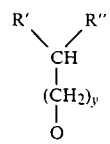

wherein R′, R″, and y are independently as defined above,
 (d)

wherein $R_5$ is independently as defined above, preferably R′—$(CH_2)_y$— wherein R′ and y are independently as defined above, (5) $R_4$ is
 (a) —$CH_2OR_7$ wherein $R_7$ is hydrogen, lower acyl, a lower alkyl,
 (b)

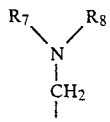

wherein $R_7$ is independently as defined above and $R_8$ is hydrogen, lower alkyl, or benzyl,
 (c)

(d) —C≡N,
 (e)

wherein $R_9$′ is hydrogen, lower alkyl or benzyl; and (6) n is independently as defined above, together with a pharmaceutically acceptable carrier.

The present invention is also directed to a pharmaceutical composition for treating hypertension in mammals comprising an antihypertensive effective amount of selected compounds of formula II which selected compounds have formula (IIa)

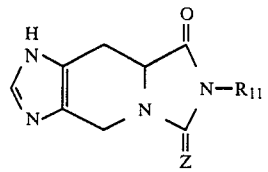

and the nontoxic, pharmaceutically acceptable base or acid addition salts thereof, wherein Z is oxygen or sulfur and $R_{11}$ is branched alkyl of from three to five carbons, inclusive, and phenyl substituted with of from one through five, preferably one through three, substituents comprising lower alkyl, halo, trifluoromethyl, hydroxy, lower alkoxy, lower acyloxy, amino, N-lower monoamino, N,N-lower dialkylamino, lower thioalkyl, lower alkylsulfonyl, or nitro; together with a pharmaceutically acceptable carrier.

Also the present invention is directed to a novel method of treating hypertension in mammals suffering therefrom comprising administering to such mammals an antihypertensive effective amount of a compound of formula I' as defined above in the description of the novel composition therefor above or an antihypertensive effective amount of a compound of formula IIa as defined in the description of the novel composition therefor.

DETAILED DESCRIPTION OF THE INVENTION

In the compounds of the formula I or of the formula II, the term alkyl of from one to twenty and one to fifteen carbons is meant to include a straight or branched alkyl group having the noted number of carbons, such as, for example, methyl, ethyl, propyl, butyl, pentyl, hexyl and the like and isomers thereof.

Halo includes particularly fluorine, chlorine or bromine.

Lower alkyl is methyl, ethyl, propyl, or butyl and isomers thereof.

Lower alkoxy is —O-alkyl wherein alkyl is lower alkyl.

Lower thioalkyl is —S-alkyl wherein alkyl is lower alkyl.

Lower acyloxy is alkyl

wherein alkyl is lower alkyl.

Lower alkylsulfonyl is alkyl

wherein alkyl is lower alkyl.

Heteroaryl is 2-, 3-, or 4-pyridyl; 1-, 2-, or 4-imidazolyl; 1-, 2-, 3-, 4-, 5-, 6- or 7-indolyl; 2-, or 3-thienyl; 2-, or 3-furyl; or 1-, 2-, or 3-pyrazolyl.

Cycloalkyl is of from four to twenty carbons, inclusive in a one, two or three saturated ring system, said ring comprising from four to eight carbons, inclusive, including monocyclo rings such as cyclobutyl, cyclopentyl, cyclohexyl and the like, or polycyclo rings such as adamantyl or norbornyl. Each ring may be unsubstituted or substituted by a straight or branched lower alkyl group.

The compounds of formula I are useful both in the free base form, in the form of base salts where possible, and in the form of acid addition salts. The three forms are within the scope of the invention. In practice, use of the salt form amounts to use of the base form. Appropriate pharmaceutically acceptable salts within the scope of the invention are those derived from mineral acids such as hydrochloric acid and sulfuric acid; and organic acids such as methanesulfonic acid, benzenesulfonic acid, p-toluenesulfonic acid, and the like, giving the hydrochloride, sulfate, methanesulfonate, benzenesulfonate, p-toluenesulfonate, and the like, respectively or those derived from bases such as suitable organic and inorganic bases. Examples of suitable inorganic bases for the formation of salts of compounds of this invention include the hydroxides, carbonates, and bicarbonates of ammonia, sodium, lithium, potassium, calcium, magnesium, aluminum, zinc, and the like.

Salts may also be formed with suitable organic bases. Bases suitable for the formation of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines, such as methylamine, dimethylamine, and triethylamine; mono-, di- or trihydroxyalkylamines such as mono-, di- and triethanolamine; amino acids such as arginine, and lysine; guanidine; N-methylglucosamine; N-methylglucamine; L-glutamine; N-methylpiperazine; morpholine; ethylenediamine; N-benzylphenethylamine; tris(hydroxymethyl)aminomethane; and the like. (See for example, "Pharmaceutical Salts," *J. Pharm. Sci.* 66 (1):1–19 (1977).)

The acid addition salts of said basic compounds are prepared either by dissolving the free base of compound I, I' or II in aqueous or aqueous alcohol solution or other suitable solvents containing the appropriate acid or base and isolating the salt by evaporating the solution, or by reacting the free base of compound I, I', or II with an acid as well as reacting compound I, I' or II having an acid group thereon with a base such that the reactions are in an organic solvent, in which case the salt separates directly or can be obtained by concentration of the solution.

The compounds of the invention may contain an asymmetric carbon atom. Thus, the invention . includes the individual stereoisomers, and the mixtures thereof. The individual isomers may be prepared or isolated by methods known in the art.

The novel processes of the present invention are described, generally, as follows:

Method A

In a process for the preparation of a compound having the formula

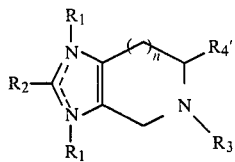

wherein $R_1$, n and $R_4$ are defined above and $R_3$ is

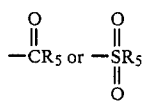

wherein $R_5$ is as defined above; a compound of formula III shown below wherein $R_1$, n, and $R_4$ are as defined above, is acylated using an appropriately activated acylating derivative of $R_5CO_2H$ or $R_5SO_3H$.

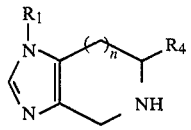
III

Preferred methods use dicyclohexylcarbodiimide to activate the $R_5CO_2H$ for reaction with a compound of formula III using modifications known in the art; or involve preparation of acylhalides such as

wherein Hal is halo, preferably chloro or bromo; or involves preparation of

wherein Hal is halo, preferably chloro or bromo, or involves preparation of mixed or symmetrical anhydrides, for reaction with a compound of formula III. The reaction is carried out in nonaqueous solvent, such as acetonitrile, tetrahydrofuran or methylene chloride, with an added organic base, such as triethylamine or pyridine, if needed at temperatures between $-10°$ C. and the reflux temperature of the solvent. Alternatively, the compound of formula III wherein $R_4$ is $CO_2H$ may be acylated in aqueous basic solution with selected compounds of the formula

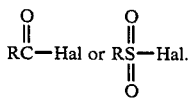

For compounds of formula I' wherein $R_4$ defined as $CO_2H$ is desired, compounds wherein $R_4$ is $COOR_9$ wherein $R_9$ is lower alkyl or benzyl may be hydrolyzed under mildly acidic or basic conditions using standard procedures known in the literature.

Compounds of formula III are obtained by reacting $\pi$-$R_1$-substituted histidine derivatives with formaldehyde or a formaldehyde equivalent such as dimethoxmethane in the presence of a strong acid such as hydrochloric acid. The reaction is carried out in aqueous medium at temperatures between 0° C. and the refluxing temperature of the solvent. Compounds III wherein $R_4$ is COOH are isolated and may be esterified using lower alkanols. The acid of formula III having $R_4$ as $COOR_9$ wherein $R_9$ is lower alkyl or benzyl may be reduced to form a compound wherein $R_4$ is $CH_2OH$ using standard methods known in the art. $\pi$-$R_1$-substituted histidines are known or may be prepared by a variety of methods known in the literature, (*Rec. Trav. Chim.*, 1972, 91, p. 246). When n is 2 then the homo histidine (Peptides Symp: Proc. 11th Eur. Peptide Symposium (1973) p. 351) is used as a starting material.

Method B

An alternative procedure for obtaining compounds of the invention having the formula I or II wherein $R_1$, $R_4$, $R_5$ and n defined in a manner corresponding to IV and V below consists of treating a compound of formula IV as shown below wherein $R_4$, $R_5$, and n are as defined above, with $R_1$-Q, wherein Q is a leaving group suitable to be an alkylating agent, such as discussed below, and then treating the intermediate salt, a compound of the formula V, wherein $R_1$, $R_4$, $R_5$ and n are as defined above, with a reducing agent, preferably zinc in an acidic medium.

The compounds of formula IV or V are as follows:

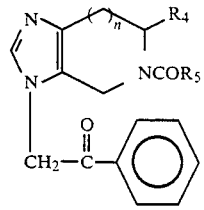
IV

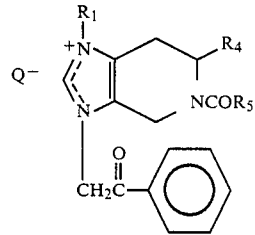
V

Suitable alkylating agents are $R_1$-Q wherein $R_1$ is as defined above and Q may be halo, or sulfonate and trifluorosulfonate esters of $R_1$-OH wherein $R_1$ is as defined above. The substituent $R_4$ of the compound of formula I may then be processed by hydrolysis as needed. This method may also be used to prepare intermediates of formula III as shown and defined above for use in Method A. In this case, the group

is removed by hydrolysis, typically under aqueous acidic conditions within the skill of the ordinary artisan. Intermediates of the formula IV as shown and defined above are prepared by a similar sequence of reactions described for the preparation of the compounds of formula III above; namely acylation of a compound of formula VI as shown below wherein $R_4$ is as defined above, which is formed by an acidic formaldehyde ring formation reaction with τ-phenacyl histidine, a compound described in the literature, (*J. Chem. Soc.*, Per I (1979) p. 2261).

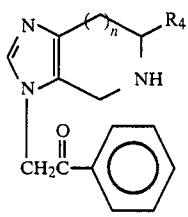

VI

Method C

Still another alternate procedure by which the compounds having formula I or formula II of this invention may be obtained, as well as intermediates III and IV cited above, consists of treating 4,5,6,7-tetrahydro-1H-imidazo[4,5-c]pyridine-6-carboxylic acid also known as spinacine or the lower alkyl ester thereof described in (Hoppe-Seyler Zeitschrift. Physiol. Chem. (1949) vol. 284, p. 129) with an isocyanate or isothiocyanate of the formula RN=C=O or RN=C=S respectively, to give a compound of the formula (VII)

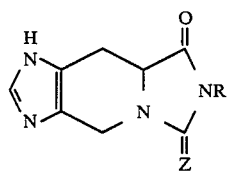

VII wherein Z and R are as defined above. Selected compounds of formula II as described in the second part of this invention are prepared in this manner and may be shown as follows:

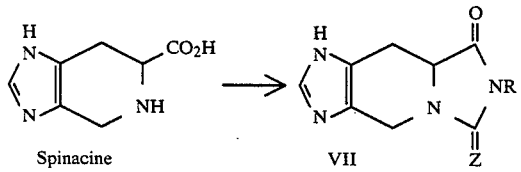

Spinacine        VII

Compounds of formula VII as defined above are then further converted to compounds of formula I, by treatment with an alkylating agent $R_1$-Q, as described in Method B, in the presence of a strong base, typically sodium or potassium hydride or sodium alkoxide in polar aprotic solvent, such as tetrahydrofuran, dimethylformamide or the like to give a mixture of a compound of formula VIII wherein Z, R, and $R_1$ are as defined above and a compound of formula IX wherein Z, $R_1$, and R are as defined above which can be separated by crystallization or chromatography.

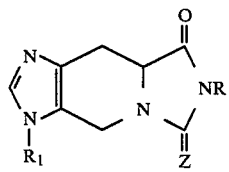

VIII

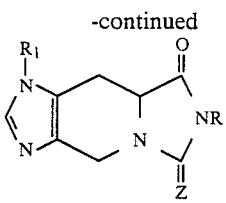

IX

The compounds of formula VIII or IX are then in turn hydrolyzed under moderate basic conditions, e.g., alkali hydroxide in aqueous alcoholic medium at reflux until solution occurs, to give compounds of formula I wherein $R_5$ is

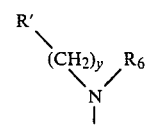

wherein R' and y are as defined above and $R_6$ is H; or under more vigorous basic conditions, e.g., concentrated alkali hydroxide treated for prolonged periods under reflux, to give intermediates of formula III wherein $R_4$ is $CO_2H$. It should be appreciated that intermediates of formula III and VI both as shown and defined above may also be directly converted to compounds of formula VIII or IX also as shown and defined above by reaction with isocyanates or isothiocyahates.

Compounds of the formula I or II of the invention wherein $R_2$ is other than H may be prepared by transformations of intermediates already described. Thus, compounds of the formula I wherein $R_2$ is H, $R_1$ is as defined above, $R_4$ is $CH_2OR_7$ and $R_3$ is $COR_5$; VIII or IX both as shown and defined above, can be treated with a brominating agent such as bromine or N-bromosuccinimide in a solvent to give a compound of formula I wherein $R_2$ is Br or a compound of the formula II wherein $R_2$ is Br. Especially useful is the intermediate of the formula X as shown and defined below,

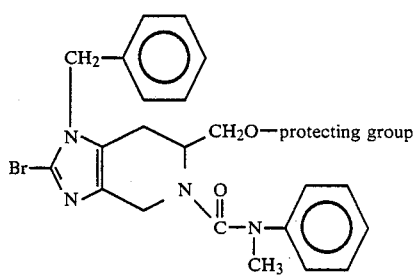

X (the preferred protecting group is trialkylsilyl) which may be further treated with an alkyllithium reagent, preferably n-butyllithium in an anhydrous solvent at low temperature to form a lithio derivative which may react with an alkylating agent $R_2$-Q, where Q is as described above, an aldehyde or ketone, or an appropriate carboxylic acid derivative to install other $R_2$ moieties as described above. Further processing of the intermediate of formula X to compounds I defined above follows the procedures disclosed under Methods A, B, or C above.

Alternatively, compounds of formula VIII or IX both as defined above wherein Z is 0, may be reacted with an aroylhalide in an aprotic solvent in the presence of a tertiary organic base such as triethylamine to give compounds of formula II where $R_2$ is A summary of the above described general methods of preparation can be shown by the following schematic.

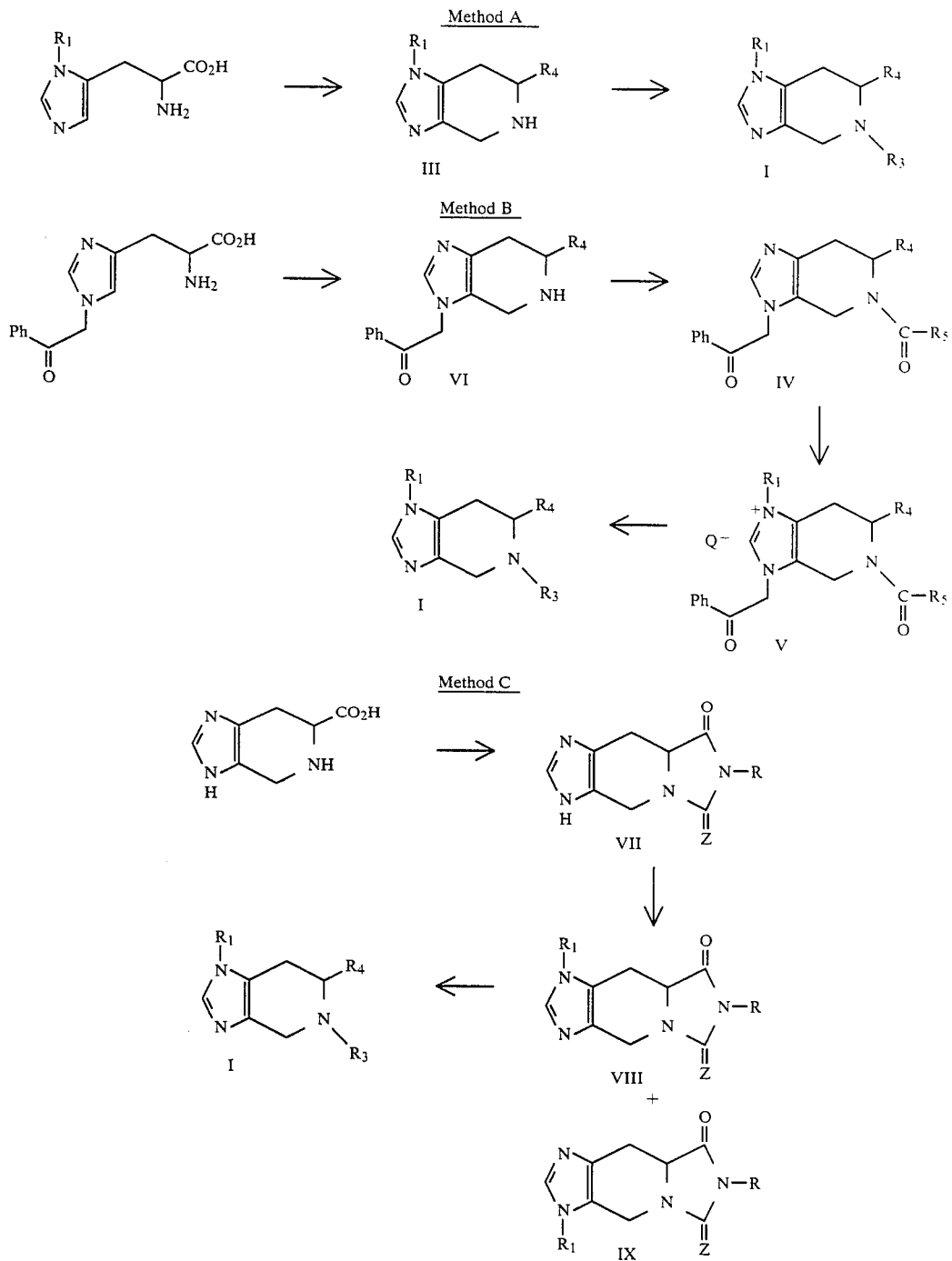

wherein R' is as defined above. This group may be further reduced and deoxygenated using methods known in the art to provide other $R_2$ substituents as defined above.

Under certain circumstances it is necessary to protect either the N or O of intermediates II and III in the above noted process with suitable protecting groups which are known. Introduction and removal of such suitable oxygen and nitrogen protecting groups are well-known in the art of organic chemistry; see for example, (1) "Protective Groups in Organic Chemistry," J. F. W. McOmie, ed., (New York, 1973), pp. 43ff, 95ff; (2) J. F. W. McOmie, *Advances in Organic Chemistry*, 3:191–281 (1963); (3) R. A. Borssonas, *Advances in Organic Chem-* istry, 3:159–190 (1963); and (4) J. F. W. McOmie, Chem. & Ind., 603 (1979).

Examples of suitable oxygen protecting groups are benzyl, t-butyldimethylsilyl, methyl, isopropyl, ethyl, tertiary butyl, ethoxyethyl, and the like. Protection of an N-H containing moiety is necessary for some of the processes described herein for the preparation of compounds of this invention. Suitable nitrogen protecting groups are benzyl, triphenylmethyl, trialkylsilyl, trichloroethylcarbamate, trichloroethoxycarbonyl, vinyloxycarbamate, and the like.

In the process described herein for the preparation of compounds of this invention the requirements for protective groups are generally well recognized by one skilled in the art of organic chemistry, and accordingly the use of appropriate protecting groups is necessarily implied by the processes of the charts herein, although not expressly illustrated.

The products of the reactions described herein are isolated by conventional means such as extraction, distillation, chromatography, and the like. Generally, the starting materials are known, can be purchased commercially, or synthesized by known methods.

The compounds of formula I and of formula IIa and the pharmaceutically acceptable base or acid addition salts thereof are useful as antihypertensive agents for the treatment of high blood pressure.

PHARMACOLOGICAL EVALUATION

The usefulness of the compounds of the present invention having formula I and IIa as antihypertensive agents is demonstrated by their effectiveness in standard pharmacological test procedures, for example, in inhibiting of $^{125}$I-angiotensin II binding or in causing a significant decrease in mean arterial blood pressure in the conscious rat either in a 2 kidney, 1-clip Goldblatt hypertensive rat (RHR) or a spontaneously hypertensive rat (SHR).

Thus, for example, compounds of formula I when administered intraperitoneally or orally to 2 kidney, 1-clip Goldblatt (renal) hypertensive rats (See S Sen, et al., "Role of Renin-Angiotensin System in Chronic Renal Hypertensive Rats," *Hypertension* 1:427–434 (1979) and *Clin. Soc.* 57:53–62, 1979, "Antihypertensive Effect of Prolonged Blockade of Angiotensin Formation in Benign and Malignant, one-and two-kidney Goldblatt Hypertensive Rats".) at doses in the range of 1–100 mg/kg cause 10–80 mmHg drops in blood pressure. Compounds of formula I have also been shown to antagonize the binding of angiotensin II to rat adrenal receptor preparations (procedure of J. G. Douglas et al., Endocrinology, 106, 120–124 (1980)). Compounds which antagonize the action of angiotensin II, an endogenous pressor peptide, are known to be effective antihypertensive agents (I. Reid., Arch. Int. Med., 145, 1475–1479 (1985); N. K. Hollenberg, Am. Rev. Pharmacol. Toxicol., 19, 559–582 (1979)). In addition, compounds of formula II, although not possessing this later property, have been shown to lower blood pressure in spontaneously hypertensive rats at doses of 1–100 mg/kg orally. This test has been shown to be a good predictor of antihypertensive activity in man (See K. O. Kamoto, ed., "Spontaneous Hypertension—Its Pathogenesis and Complications", Igaku Shoin Ltd., Tokyo, Springer Verlag, Berlin, Heidelbert, N.Y. and H. J. Baker et al, ed., *The Laboratory Rat Vol II.* "Research Applications", American College of Laboratory Animal Medicine Series, Academic Press, 1980, pp. 168–170.).

Angiotensin binding inhibition activity and blood pressure lowering activity in renal hypertensive rats of the optimally substituted examples of formula I are listed in Table 1. Blood pressure lowering activity in spontaneously hypertensive rats of optimally substituted examples of formula II are listed in Table 2.

Specifically, the protocol for the test procedures resulting in the data of Tables 1 and 2 is as follows:

ANTIHYPERTENSIVE EVALUATION (AHP3)

A Method for the Direct Monitoring of Aortic Blood Pressure and Heart Rate from Conscious Rats The continuous monitoring of pulsatile blood pressure (BP) from unrestrained conscious rats surgically equipped with polyethylene cannulas was accomplished by means of a computer assisted data capture scheme (CADCS). The basic elements of the methodology are the cannulation procedure and the CADCS.

Method

Cannulation Procedure:

Rats were anesthetized with Telazol (1:1 tiletamine HCl and zolazepam HCl); 20–40 mg/kg IM and the descending aorta exposed via a midline incision. Cannulas fabricated from polyethylene tubing were inserted into the aorta via an undersized puncture hole below the renal arteries. The puncture hole was made by a 23 G disposable needle with a section of the aorta clamped off above and below the puncture site. The cannulas, consisting of a PE100 (0.86 mm ID) body and a PE50 (0.58 mm ID) tip, were attached to a trocar, inserted through the psoas muscle, and passed subcutaneously along the midline of the back and externalized between the ears. The cannulas were anchored to the psoas muscle and between the scalulae (3-0 green braided suture). The midline incision was closed in two steps (muscle first, skin second) using continuous over-and-over sutures (4-0 chronic). Each rat was then given penicillin 30,000 units subcutaneously (Penicillin G Procaine Sterile Suspension).

The rats were fitted with a harness-springswivel assembly designed to protect the cannula and to provide the rat relative freedom of movement. The harnesses were fabricated from nylon hook and loop tape cemented to a metal plate to which spring wires (18-8 stainless steel), were attached to brass swivels. Each polyethylene cannula was channeled through a spring and connected through a swivel to a pressure transducer (Model P23Gb; Statham Instruments; Hato Rey, Puerto Rico) and an infusion pump (Sage model 234-7; Orion Research, Cambridge, Mass.) by means of PE100 tubing. While on test, each rat received a continuous slow infusion of heparinized saline solution (approximately 0.40 ml or 40 units of heparin per 24 hr period) to prevent clot formation. Additional "flushes" of the cannula with heparinized saline were carried out when the aortic pulse pressure (systolic minus diastolic) was less than 25 mm Hg.

CADCS:

The pulsatile blood pressure of each of 32 rats was monitored continuously by two signal conditioning units (Gould, Clev., Ohio). The signals from these units were monitored and digital data for mean, systolic, and diastolic blood pressures as well as for heart rate were calculated every 5 min by two in-laboratory computers (Hewlett Packard, Cupertino, Calif.). These in-laboratory computers have the capacity to store 32 days of this 5 min data. Communication with the mainframe research computer (IBM 3083) from the two inlaboratory computers allowed for data analysis and report generation. The overall scheme involved modulating the primary signal from the pressure transducer, calculating the 5 min data values for mean, systolic, and diastolic blood pressures as well as heart rate by the in-laboratory computers and generating summary data on the mainframe research computer.

In order to monitor the effects of drugs on blood pressure or heart rate, either spontaneously hypertensive rats (SHR) or renin-dependent 2 kidney, 1-clip Goldblatt hypertensive rats (RHR) were dosed intraperitoneally or orally with test compounds. Rats were dosed once daily for up to 3 consecutive days and hemodynamic variables were continuously monitored for up to 24 hr following the last day of dosing.

and a method for treating hypertension comprising administering to mammals, including humans, suffering therefrom either orally or parenterally the corresponding pharmaceutical composition. The composition contains a compound of the formula I' or the formula IIa each as defined above in appropriate unit dosage form.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active

TABLE I
ANTI HYPERTENSIVE ACTIVITY OF COMPOUNDS OF FORMULA I

| EXAMPLE Number | $R_1$ | $R_3$ | $R_4$ | $IC_{50}(\mu M)$* | Max % decrease in blood pressure 30 mg/kg ip in RHR** |
|---|---|---|---|---|---|
| 169 | $CH_2Ph$ | $COCHPh_2$ | $CO_2H$ | 1.0 | −20 |
| 22 | $CH_2Ph$ | $COCH(Ph-4Cl)_2$ | $CO_2H$ | 6.8 | −27 |
| 29 | $CH_2Ph$ | CO(9-fluorenyl) | $CO_2H$ | 8.0 | −22 |
| 13 | $CH_2((4-NH_2, 3-Me)Ph)$ | $COCHPh_2$ | $CO_2H$ | 0.06 | −22 |
| 278 | $CH_2Ph$ | CON(Me)Ph | $CH_2OH$ | 1.6 | −22 |
| 2 | $CH_2CH_2$—(1-adamantyl) | $COCHPh_2$ | $CO_2H$ | 0.10 | −26 |
| 21 | $CH_2(4-CF_3Ph)$ | $COCHPh_2$ | $CO_2H$ | 0.19 | −18 |
| 4 | $CH_2CH_2$—cyclohexyl | $COCHPh_2$ | $CO_2H$ | 0.24 | −13 |
| 75 | $CH_2(3-CH_3Ph)$ | $COCHPh_2$ | $CO_2H$ | 0.27 | −30 |
| 279 | $CH_2((4-OCH_3, 3-Me)Ph)$ | $COCHPh_2$ | $CH_2OH$ | 0.37 | −25 |
| 17 | $CH_2(2-OHPh)$ | $COCHPh_2$ | $CO_2H$ | 0.69 | −21 |
| 24 | $CH_2((4-OMe, 3Me)Ph)$ | COCH(Ph)cyclohexyl | $CO_2H$ | 0.07 | −16 |
| 26 | $CH_2((4-OMe, 3Me)Ph)$ | $COCH_2$cyclohexyl | $CO_2H$ | 2.0 | −18 |
| 23 | $CH_2Ph$ | $COCH(Ph-4F)_2$ | $CO_2H$ | 2.1 | −22 |
| 19 | $CH_2((4-OMe, 3Me)Ph)$ | $COCHPh_2$ | $CO_2H$ | 0.07 | −14 |
| 6 | $CH_2CH_2Ph$ | $COCH_2Ph$ | $CO_2H$ | 2.4 | −16 |
| 25 | $CH_2((4-OMe, 3Me)Ph)$ | $COCH(Ph-4Me)_2$ | $CO_2H$ | 0.51 | −12 |

*$IC_{50}(\mu M)$ for inhibition of $^{125}$I-angiotensin II binding to rat adrenal receptor preparations.
**RHR = 2 kidney, 1-clip Goldblatt hypertensive rat.

TABLE II
ANTI HYPERTENSIVE ACTIVITY OF COMPOUNDS OF FORMULA II

| EXAMPLE Number | $R_1$ | $R_5$ | X | Max % decrease in blood pressure 30 mg/kg PO in SHR* |
|---|---|---|---|---|
| 158 | H | Ph(4-SMe) | O | −17 |
| 155 | H | Ph(4-OMe) | O | −39 |
| 157 | H | Ph(2,4-(OMe)$_2$) | O | −22 |
| 154 | H | iPr | O | −39 |
| 156 | H | tBu | O | −18 |
| 162 | H | iPr | S | −39 |
| 161 | H | Ph | S | −28 |
| 159 | H | Ph(4-OMe) | S | −39 |
| 160 | H | Ph(4-NMe$_2$) | S | −34 |
| 129 | 3-$CH_3$ | iPr | O | −36 |
| 130 | 1-$CH_2Ph$ | iPr | O | −21 |
| 128 | 1-$CH_2Ph$ | Ph(4-OMe) | S | −32 |
| 133 | 1-$CH_2Ph$ | Ph(4-OMe) | O | −29 |
| 127 | 1-$CH_2((4-OMe, 3Me)Ph)$ | Ph(4-OMe) | S | −24 |
| 273 | 1-$CH_2((4-NO_2, 3Me)Ph)$ | Ph(4-OMe) | O | −14 |

*Spontaneously hypertensive rat

Accordingly, the present invention also includes a pharmaceutical composition for treating hypertension compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single licuid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 0.1 mg to 500 mg preferably to 1 to 100 mg according to the particular application and the potency of the active ingredient. The compositions can, if desired, also contain other compatible therapeutic agents.

In therapeutic use as described above, the mammalian dosage range for a 70 kg subject is from 0.1 to 150 mg/kg of body weight per day or preferably 1 to 100 mg/kg of body weight per day. The dosages, however, may be varied depending upon the requirements of the patient, the severity of the condition being treated, and the compound being employed.

Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following Examples further illustrate the invention, but without, however, limiting it thereto.

The following examples specifically illustrate generally Methods A, B and C as described above.

METHOD A

EXAMPLE 1

Methyl-1-(2-(1-adamantyl)ethyl)-5-diphenylacetyl)-4,5,6,7-tetrahydro-1H-imidazo[4,5-c]pyridine-6-carboxylate.

A solution of 11.8 mL trifluoromethanesulfonic anhydride in 70 mL dichloromethane is chilled to −70° C. and treated dropwise with a solution composed of 12.6 g 1-adamantyl-2-hydroxyethane, 12.2 mL diisopropylethylamine and 70 mL dichloromethane. The solution is allowed to warm to −55° C. over 45 min then a solution of 25 g N,1-bis-BOC-histidine methyl ester (J. Chem. Soc., Perkin Trans. I 1982; 1553-61.) in 70 mL dichloromethane is added dropwise. The reaction is then stirred at 25° C. for 24 hr and poured into pH=7, 0.25M potassium phosphate buffer (500 mL), stirring vigorously. The organic layer is separated, washed with the same buffer, dried and concentrated. 3-(2-(1-Adamantyl)ethyl)-N-BOC-histidine methyl ester is isolated by chromatography on silica gel (chloroform-methanol, 99:1) as a gum. NMR (CDCl$_3$) 3.85 (m,2H,NCH$_2$).

A portion of the above product (8.4 g) is treated with 350 mL 6N HCl, heating at reflux 2.5 hr. Evaporation gives 3-(2-(1-adamantyl)ethyl)histidine dihydrochloride as a glass. NMR (D$_2$O) 8.85 (s,1H,2-Im); 7.55 (s,1H,5-Im).

A solution of 7.8 g 3-(2-(1-adamantyl)ethyl)histidine.2HCl in 100 mL 1N HCl is treated with 5 mL 36% formaldehyde, stirring 30 min at 25° C. followed by 90 min at reflux. Evaporation gives 1-(2-(1-adamantyl)ethyl)-4,5,6,7-tetrahydro-1H-imidazo[4,5-c]-pyridine-6-carboxylic acid dihydrochloride as a white solid. NMR (D$_2$O) 8.90 (s,1H,2-Im).

A solution of 8.0 g of the above carboxylic acid in 350 mL methanol is treated with 35 mL trimethyl orthoformate, saturated with anhydrous HCl and heated at reflux 6 hr. The resulting solution is evaporated to a foam, suspended in 350 mL dichloromethane and treated dropwise with 350 mL cold 10% Na$_2$CO$_3$. The organic layer is separated, dried and evaporated to give methyl-1-(2-(1-adamantyl)ethyl)-4,5,6,7-tetrahydro-1H-imidazo[4,5-c]-pyridine-6-carboxylate as a gum. NMR (D$_2$O+DCl) 4.08 (s,3H,CO$_2$Me).

A mixture of 1.1 g dicyclohexycarbodiimide, 1 10 g hydroxybenzotriazole hydrate, 1.1 g diphenylacetic acid and 25 mL acetonitrile is stirred at 25° C. for 10 min then treated with a solution of 2.0 g methyl-1-(2-(1-adamantyl)ethyl)-4,5,6,7-tetrahydro-1H-imidazo[4,5-c]-pyridine-6-carboxylate in 25 mL acetonitrile. The resulting suspension is stirred 48 hr at 25° C., filtered and the filtrate is evaporated, dissolved in dichloromethane, washed with 10% Na$_2$CO$_3$, dried and evaporated. Chromatography on silica gel (chloroform) gives a yield of methyl-1-(2-adamantyl)ethyl)-5-diphenylacetyl-4,5,6,7-tetrahydro-1H-imidazo[4,5-c]-pyridine-6-carboxylate. NMR (CDCl$_3$) 3.63 (s,3H,CO$_2$Me), 5.35 (s,1H,CHPh$_2$).

EXAMPLE 2

1-(2-(1-Adamantyl)ethyl)-5-diphenylacetyl-4,5,6,7-tetrahydro-1H-imidazo[4,5-c]pyridine-6-carboxylic acid.

A solution of 2.0 g methyl-1-(2-(1-adamantyl)ethyl)-5-diphenylacetyl-4,5,6,7-tetrahydro-1H-imidazo-[4,5-c]-pyridine-6-carboxylate in tetrahydrofuranmethanol (3:1, 20 mL) is treated at 25° C. with 4.1 mL 1N NaOH. After 6 hr the solution is evaporated, the residue is suspended in 10 mL water and treated with 4.1 mL 1N HCl. The resulting precipitate is collected by filtration and dried to afford a white solid, 1-(2-(1-adamantyl)ethyl)-5-diphenylacetyl-4,5,6,7-tetrahydro-1H-imidazo[4,5-c]pyridine-6-carboxylic acid. MS (FAB) 524 (M+1). mp 168°-175° C. or 187° to 200° C. dec.

EXAMPLE 3

Methyl-1-(2-cyclohexylethyl)-5-diphenylacetyl-4,5,6,7-tetrahydro-1H-imidazo[4,5-c]pyridine-6-carboxylate.

By substituting 2-cyclohexylethanol for 1-adamantyl-2-hydroxyethane in Example 1, one obtains this adduct. NMR (CDCl$_3$) 3.81 (t,2H,NCH$_2$).

EXAMPLE 4

1-(2-Cyclohexylethyl)-5-diphenylacetyl-4,5,6,7-tetrahydro-1H-imidazo[4,5-c]pyridine-6-carboxylic acid.

The methyl ester from Example 3 is saponified using the procedure described in Example 2 to give this acid as a white solid. MS (FAB) 472 (M+1). mp 137°-140° C.

EXAMPLE 5

Methyl-1-(2-phenylethyl)-5-phenylacetyl-4,5,6,7-tetrahydro-1H-imidazo[4,5-c]pyridine-6-carboxylate.

By substituting 2-phenylethanol for 1-adamantyl-2-hydroxyethane and phenylacetic acid for diphenylacetic acid in Example 1, one obtains this adduct. NMR (CDCl$_3$) 4.08 (d of t,2H,NCH$_2$).

EXAMPLE 6

1-(2-Phenylethyl)-5-phenylacetyl-4,5,6,7-tetrahydro-1H-imidazo[4,5-c]pyridine-6-carboxylic acid.

The methyl ester from Example 5 is saponified using the procedure described in Example 5 to give this acid as a white solid. MS (DEI) 389 (M). mp 215°-220° C.

In a process analogous to Examples 1 through 6 above and also as generally described in Method A above using appropriate starting materials the corresponding compounds of formula I are prepared.

EXAMPLE 7

1H-Imidazo[4,5-c]pyridine-6-carboxylic acid, 4,5,6,7-tetrahydro-1-(3-methylbutyl)-5-(phenylacetyl)-, (S)-; mp 168°-171° C.

EXAMPLE 8

1H-Imidazo[4,5-c]pyridine-6-carboxylic acid, 1-(2-cyclohexylethyl)-4,5,6,7-tetrahydro-5-(phenylacetyl)-, (S)- (R$_1$ is cyclohexylethyl); mp 200°-205° C.

EXAMPLE 9

1H-Imidazo[4,5-c]pyridine-6-carboxylic acid, 5-[bis(4-fluorophenyl)acetyl]-1-(2-cyclohexylethyl)-4,5,6,7-tetrahydro-, (S)-; mp 144°-149° C.

EXAMPLE 10

1H-Imidazo[4,5-c]pyridine-6-carboxylic acid, 5-(cyclohexylacetyl)-1-(2-cyclohexylethyl)-4,5,6,7-tetrahydro-, (S)-; MS (DEI) 401 (m).

EXAMPLE 11

Methyl-1-(3-methyl-4-nitrophenyl)methyl-5-diphenylacetyl-4,5,6,7-tetrahydro-1H-imidazo[4,5-c]-pyridine-6-carboxylate.

A solution of 5.55 mL trifluoromethanesulfonic anhydride in 50 mL dichloromethane is chilled to −75° C. and treated dropwise with a solution composed of 5.52 g 3-methyl-4-nitrobenzyl alcohol, 5.75 mL diisopropylethylamine and 50 mL dichloromethane. The resulting mixture is stirred 30 min at −75° C. then treated dropwise with a solution of N,1-bis-BOC-histidine methyl ester[1] in 50 mL dichloromethane. The reaction mixture is allowed to warm to 25° C. over 16 hr and poured into pH=7, 0.25M potassium phosphate buffer (300 mL), stirring vigorously. Organic layer is washed with the same buffer, dried and concentrated. 3-(4-Methyl-3-nitrophenyl)methyl-n-BOC-histidine methyl ester is isolated by chromatography on silica gel (chloroform-methanol, 99:1) as a gum. NMR (CDCl$_3$) 2.55 (s,3H,ArMe); 1.34 (s,9H,t-Bu).

Hydrolysis of the above gum in refluxing 6N HCl affords 3-(3-methyl-4-nitrophenyl)methylhistidine dihydrochloride which is treated with formaldehyde and esterified as in Example 1 to give methyl-1-(3-methyl-4-nitrophenyl)methyl-4,5,6,7-tetrahydro-1H-imidazo[4,5-c]pyridine-6-carboxylate as a solid. NMR (CDCl$_3$) 5.08 (s,2H,CH$_2$Ar).

A mixture of 16.7 g dicyclohexycarbodiimide, 10.9 g hydroxybenzotriazole hydrate, 17.2 g diphenylacetic acid and 150 mL acetonitrile is stirred at 2° C. for 15 min then treated with a solution of 25.4 g methyl-1-(3-methyl-4-nitrophenyl)methyl-4,5,6,7-tetrahydro-1H-imidazo[4,5-c]pyridine-6-carboxylate in 125 mL acetonitrile. The resulting suspension is stirred 48 hr at 25° C., filtered and the filtrate is evaporated, dissolved in dichloromethane, washed with 10% Na$_2$CO$_3$, dried and evaporated. Chromatography on silica gel (chloroform-methanol, 99:1) gives a crisp foam which crystallizes when triturated with methanol. MS (FAB) 525 (M+1).

EXAMPLE 12

Methyl-1-(4-amino-3-methylphenyl)methyl-5-diphenylacetyl-4,5,6,7-tetrahydro-1H-imidazo[4,5-c]pyridine-6-carboxylate.

A solution of 31.2 g methyl-1-(4-nitro-3-methylphenyl)methyl-5-diphenylacetyl-4,5,6,7-tetrahydro-1H-imidazo[4,5-c]pyridine-6-carboxylate in tetrahydrofuran-methanol (2:1, 600 mL) is treated with 8.0 g Raney Nickel and placed under an atmosphere of hydrogen at 50 psi for 26 hr. The catalyst is removed by filtration and filtrate is evaporated to give a crisp foam. NMR (CDCl$_3$) 6.77 (s+d,2H,2,6-Ar); 6.60 (d,1H,5-Ar). mp 182°–188° C.

EXAMPLE 13

1-(4-Amino-3-methylphenyl)methyl-5-diphenylacetyl-4,5,6,7-tetrahydro-1H-imidazo[4,5-c]pyridine-6-carboxylic acid.

The methyl ester from Example 12 is saponified using the procedure described in Example 2 to give this acid as a white solid. MS (FAB) 481 (M+1).

EXAMPLE 14

Methyl-1-(4-dimethylamino-3-methylphenyl)-methyl-5-diphenylacetyl-4,5,6,7-tetrahydro-1H-imidazo[4,5-c]pyridine-6-carboxylate.

A solution of 2.9 g methyl-1-(4-amino-3-methylphenyl)methyl-5-diphenylacetyl-4,5,6,7-tetrahydro-1H-imidazo[4,5-c]pyridine-6-carboxylate in 150 mL ethanol is treated consecutively with 2.5 mL 36% formaldehyde, 12 mL 1N HCl and 1.2 g NaCNBH$_3$. After 20 min addition of an additional 12 mL 1N HCl is begun via syringe pump over a 5 hr period. The reaction mixture is stirred an additional 1 hr then evaporated. The residue is partitioned between dichloromethane and 5% Na$_2$CO$_3$ (100 mL each) and the organic layer is dried and evaporated. The major product is isolated by chromatography on silica gel (chloroform-methanol, 99.5:0.5) as a crisp foam upon evaporation of solvents. NMR (CDCl$_3$) 2.67 (s,6H,N(Me)$_2$). mp 165° C.

EXAMPLE 15

1-(4-Dimethylamino-3-methylphenyl)methyl-5-diphenylacetyl-4,5,6,7-tetrahydro-1H-imidazo[4,5-c]pyridine-6-carboxylic acid.

The methyl ester from Example 14 is saponified using the procedure described in Example 2 to give this acid as a white solid. MS (FAB) 509 (M+1); 1017 (2M+1). mp 72°–75° C.

EXAMPLE 16

Ethyl-1-(2-hydroxyphenyl)methyl-5-diphenyl-acetyl-4,5,6,7-tetrahydro-1H-imidazo[4,5-c]pyridine-6-carboxylate.

A solution of 8 g methanesulfonic anhydride in 45 mL dichloromethane is chilled to −50° C. and treated dropwise with a solution of 6.2 mL 2-methoxybenzyl alcohol, 8.0 mL diisopropylethylamine and 45 mL dichloromethane. The resulting solution is warmed to 0° C. over 30 min and treated dropwise with 15.0 g N,1-bis-BOC-histidine methyl ester dissolved in 45 mL dichloromethane. The mixture is then heated at reflux 24 hr, poured into 400 mL 0.25M, pH=7 potassium phosphate buffer and the organic layer is separated, dried and evaporated. Chromatography on silica gel, eluting with chloroform-methanol (99:1) gives 3-(2-methoxyphenyl)-methyl-N-BOC-histidine methyl ester as a gum. NMR (CDCl$_3$) 4.96 (s,2H,NCH$_2$Ar).

The above gum is treated with 150 mL 6N HCl at reflux for 3 hr, evaporated to a gum and triturated with ethanol to afford 3-(2-methoxyphenyl)methylhistidine dihydrochloride as a colorless solid. MS (FAB) 267 (M+1); 551 (2M+1).

The above solid (3.7 g) is dissolved in 40 mL water and treated with 2.5 mL 36% formaldehyde, stirring 30 min at 25° C. followed by 90 min at reflux. Evaporation gives a gum which is crystallized from ethanol-isopropanol to give 1-(2-methoxyphenyl)methyl-4,5,6,7-tetrahydro-1H-imidazo[4,5-c]pyridine-6-carboxylic acid dihydrochloride as a colorless solid. NMR (D$_2$O) 3.95 (s,3H,OMe).

A solution of 2.85 g of the above carboxylic acid in concentrated HBr is heated at reflux 6 hr, diluted with 100 mL water and evaporated to afford 1-(2-hydroxyphenyl)methyl-4,5,6,7-tetrahydro-1H-imidazo-[4,5-c]pyridine-6-carboxylic acid dihydrobromide as an orange colored solid. NMR (D$_2$O) lacks the MeO singlet described above.

The crude acid is esterified by treatment with absolute ethanol and HCl at reflux. The ethanolic solution is concentrated and added dropwise to vigorously stirred ethyl acetate. Ethyl 1-(2-hydroxyphenyl)-methyl-4,5,6,7-tetrahydro-1H-imidazo[4,5-c]pyridine-6-carboxylate hydrochloride hydrobromide is collected by filtration as an off-white, hygroscopic solid. NMR (D$_2$O) 1.33 (t,3H,CH3).

A solution of the above ethyl ester, 3.8 mL diisopropylethylamine, 1.5 g imidazole and 60 mL acetonitrile is treated with 3.3 g t-butyldimethylsilyl chloride and stirred 7 hr at 25° C.

The reaction mixture is treated with 10 mL methanol, evaporated and partitioned between ethyl acetate and 10% Na$_2$CO$_3$. The organic layer is dried, evaporated and purified by chromatography on silica gel, eluting with chloroform-methanol (98:2) to give ethyl 1-(2-t-butyldimethylsiloxyphenyl)methyl-4,5,6,7-tetrahydro-1H-imidazo[4,5-c]pyridine-6-carboxylate as a gum. NMR (CDCl$_3$) 1.03 (s,9H,t-Bu).

A mixture of 1.3 g dicyclohexylcarbodiimide, 0.8 g hydroxybenzotriazole hydrate, 1.3 g diphenylacetic acid and 25 mL acetonitrile is stirred for 10 min then treated with a solution of the above silyl ether (2.4 g) in 25 mL acetonitrile. The resulting suspension is stirred at 25° C. 48 hr and filtered. The filtrate is evaporated, partitioned between dichloromethane and 10% Na$_2$CO$_3$ and the organic layer is dried and evaporated. Chromatography of the residue on silica gel, eluting with chloroform gives ethyl 1-(2-t-butyldimethylsiloxyphenyl)methyl-5-diphenylacetyl-4,5,6,7-tetrahydro-1H-imidazo[4,5-c]-pyridine-6-carboxylate as a gum. NMR (CDCl) 5.39 (s,1H,COCHAr$_2$).

The above compound is dissolved in 50 mL acetonitrile, treated with 0.65 mL 48% HF and stirred 6 hr at 25° C. The solution is then treated with 15.6 mL 1N NaOH, diluted with ethyl acetate and washed with saturated NaCl. Organic layer is dried, evaporated and chromatographed on silica gel (CHCl$_3$) to give ethyl 1-(2-hydroxyphenyl)methyl-5-diphenylacetyl-4,5,6,7-tetrahydro-1H-imidazo[4,5-c]-pyridine-6-carboxylate as a gum. NMR (CDCl$_3$) 9.68 (broad,1H,ArOH).

EXAMPLE 17

1-(2-Hydroxyphenyl)methyl-5-diphenylacetyl-4,5,6,7-tetrahydro-1H-imidazo[4,5-c]pyridine-6-carboxylic acid.

A solution of the product from Example 16 (2.35 g) in 25 mL THF-methanol (2:1) is treated with 10 mL 1N NaOH, stirring 90 min at 25° C. After treatment with 10 mL 1N HCl, the mixture is diluted with 60 mL methanol-water (2:1) and concentrated in vacuo until a thick slurry forms. The slurry is diluted with water and the desired carboxylic acid is collected by filtration. MS (FAB) 468 (M+1); mp 187°–190° C.

EXAMPLE 18

Methyl-1-(3-methyl-4-methoxyphenyl)methyl-5-diphenylacetyl-4,5,6,7-tetrahydro-1H-imidazo[4,5-c]-pyridine-6-carboxylate.

A solution of 10.8 g methanesulfonic anhydride in 120 mL dichloromethane is chilled to $-50°$ C. and treated dropwise with a solution of 9.4 g 3-methyl-4-methoxybenzyl alcohol, 10.8 mL diisopropylethylamine and 80 mL dichloromethane. The resulting solution is warmed to -25° C. over 30 min and treated dropwise with 20.0 g N,1-bis-BOC-histidine methyl ester dissolved in 125 mL dichloromethane. The mixture is then allowed to warm to 25° C. over 4 hr, stirring at this temperature 24 hr. The reaction mixture is poured into 700 mL 0.25M, pH=7 potassium phosphate buffer and the organic layer is separated, dried and evaporated. Chromatography on silica gel, eluting with chloroformmethanol (99:1) gives 3-(3-methyl-4-methoxyphenyl)methyl-N-BOC-histidine methyl ester as a gum. NMR (CDCl$_3$) 1.43 (s,9H,t-Bu).

The remainder of the synthesis proceeds as described in Example 1, using the appropriate quantities of reagents to afford methyl 1-(3-methyl-4-methoxyphenyl)-methyl-5-diphenylacetyl-4,5,6,7-tetrahydro-1H-imidazo[4,5-c]pyridine-6-carboxylate as a gum. NMR (CDCl$_3$) 4.91 (d,2H,CH$_2$Ar).

EXAMPLE 19

1-(3-Methyl-4-methoxyphenyl)methyl-5-diphenylacetyl-4,5,6,7-tetrahydro-1H-imidazo[4,5-c]-pyridine-6-carboxylic acid.

The ester product from Example 18 is converted to this acid using the procedure described in Example 2. MS (FAB) 496 (M+1); mp 222°–225° C.

EXAMPLE 20

Methyl-1-(4-trifluoromethylphenyl)methyl-5-diphenylacetyl-4,5,6,7-tetrahydro-1H-imidazo[4,5-c]-pyridine-6-carboxylate.

Substitution of 4-trifluoromethylbenzyl alcohol for 3-methyl-4-nitrobenzyl alcohol in Example 11 gives this product. NMR (CDCl$_3$) 5.06 (s,2H,CH$_2$Ar).

EXAMPLE 21

1-(4-Trifluoromethylphenyl)methyl-5-diphenylacetyl-4,5,6,7 tetrahydro-1H-imidazo[4,5-c]pyridine-6-carboxylic acid.

Hydrolysis of the ester from Example 20 according to the procedure given in Example 2 affords this acid. MS (FAB) 520 (M+1).

EXAMPLE 22

(S)-5-[bis(4-chlorophenyl)acetyl]-4,5,6,7-tetrahydro-1-(phenylmethyl)-1H-imidazo[4,5-c]pyridine-6-carboxylic acid.

To 1.3 g of dicyclohexylcarbodiimide in 20 mL of acetonitrile is added 1.7 g of bis-(4-chlorophenyl) acetic acid followed by 0.8 g of 1-hydroxybenzotriazole hydrate. This mixture is stirred 20 min at room temperature at which point 2.0 g of the dihydrochloride salt of 1-benzylspinacine methyl ester is added followed by 2.0 mL of triethylamine. This mixture is stirred for 2 hr at room temperature, filtered, concentrated and diluted with ethyl acetate. The solution is washed twice with water and once with saturated sodium bicarbonate, dried, filtered and concentrated. The resulting oil is chromotographed on silica gel eluting with 10% acetone in chloroform to afford 1.60 g (52%) of the desired amide ester, Rf=0.35 (10% acetone/chloroform).

This amide ester is then diluted in 10 mL of tetrahydrofuran and 3.0 mL of an aqueous 1M sodium hydroxide solution is added. After stirring for 3 hr at room temperature, 3.0 mL of an aqueous 1M hydrogen chloride solution is added. The solution is concentrated and the residue is triturated with water. The solid is collected by filtration and dried to afford 1.30 g of the (S)-5-[bis(4-chlorophenyl)acetyl]-4,5,6,7-tetrahydro-1-(phenylmethyl)-1H-imidazo[4,5-c]pyridine-6-carboxylic acid product, mp 162°–170° C.

EXAMPLE 23

(S)-5-[bis(4-fluorophenyl)acetyl]-4,5,6,7-tetrahydro-1-(phenylmethyl)-1H-imidazo[4,5-c]pyridine-6-carboxylic acid.

This compound is prepared following the procedure of Example 22 and using bis-(4-fluorophenyl)acetic acid as starting material. The product is a white solid with $[\alpha]_D^{20} = 11.3°$ (0 96%, methanol).

EXAMPLE 24

(S)-5-(cyclopentylphenylacetyl)-4,5,6,7-tetrahydro-1-[(4-methoxy-3-methylphenyl)methyl]-1H-imidazo-[4,5-c]pyridine-6-carboxylic acid.

This compound is prepared following the procedure of Example 22 and using cyclopentyl phenyl acetic acid as starting material. The product has mp 190° C. (dec).

EXAMPLE 25

(S)-[bis(4-methylphenyl)acetyl]-4,5,6,7-tetrahydro-1-[(4-methoxy-3-methylphenyl)methyl]-1H-imidazo[4,5-c]-pyridine-6-carboxylic acid.

This compound is prepared following the procedure of Example 22 and using bis-(4-methylphenyl)acetic acid as staring material. The product is a white solid with $[\alpha]_D^{20} = 4.9°$ (1.09%, methanol).

EXAMPLE 26

(S)-5-(cyclohexylacetyl)-4,5,6,7-tetrahydro-1-[(4-methoxy-3-methylphenyl)methyl]-1H-imidazo-[4,5-c]-pyridine-6-carboxylic acid.

This compound is prepared following the procedure of Example 22 and using cyclohexylacetic acid as starting material. The product is a white solid, m/e=426.1 (FAB).

EXAMPLE 27

5-[(9H-Fluoren-9-yl)carbonyl]-4,5,6,7-tetrahydro-1-(phenylmethyl)-1H-imidazo[4,5-c]pyridine-6-carboxylic acid.

A solution of 2.3 g of fluorene-9-carbonyl chloride in acetonitrile (25 mL) is added slowly to a solution of I base, 2.7 g of 1-benzylspinacine methyl ester; the methyl ester of the compound of Example 152 hereinafter, 1.5 g of triethyl amine and acetonitrile (25 mL) at room temperature. After 1 hr the separated triethylamine hydrochloride is filtered and the filtrate is concentrated at reduced pressure to remove solvent. Water (50 mL) is added to the residue and the insoluble gum is extracted with ethyl acetate (100 mL). The solution is dried ($Na_2SO_4$) and concentrated to give the methyl ester of the title product. This material is hydrolyzed directly.

The ester is dissolved in methanol (50 mL). 1N-Sodium hydroxide (20 mL) is added and the solution is maintained at reflux for 10 min. 1N-Hydrochloric acid (20 mL) is added to precipitate the product. Recrystallization from dimethylformamide-water gives a pure sample, mp 229°–231° C.

In a process analogous to Examples 11 through 27 above and also as generally described in Method A above using appropriate starting materials the corresponding compounds of formula I are prepared as follows:

EXAMPLE 28

1H-Imidazo[4,5-c]pyridine-6-carboxylic acid, 4,5,6,7-tetrahydro-5-[(methylphenylamino)carbonyl]-1-(phenylmethyl)-; mp 173°–180° C.

EXAMPLE 29

1H-Imidazo[4,5-c]pyridine-6-carboxylic acid, 5-[(9H-fluoren-9-yl)carbonyl]-4,5,6,7-tetrahydro-1-(phenylmethyl)-, (+)—; mp 229°–231° C.

EXAMPLE 30

1H-Imidazo4,5-c]pyridine-6-carboxylic acid, 5-(diphenylacetyl)-4,5,6,7-tetrahydro-1-(phenylmethyl)-, (S)-; mp 220°–225° C. (dec).

EXAMPLE 31

1H-Imidazo[4,5-c]pyridine-6-carboxylic acid, 4,5,6,7-tetrahydro-5-(phenylacetyl)-1-(phenylmethyl)-, (S)-; mp 215°–217.5° C. (dec).

EXAMPLE 32

1H-Imidazo[4,5-c]pyridine-6-carboxylic acid, 4,5,6,7-tetrahydro-5-[(4-methoxyphenyl)acetyl]-1-(phenylmethyl)-, monohydrochloride, (S)-; mp 195° C. (dec).

EXAMPLE 33

1H-Imidazo[4,5-c]pyridine-6-carboxylic acid, 4,5,6,7-tetrahydro-5-[(3-methoxyphenyl)acetyl]-1-(phenylmethyl)-, monohydrochloride, (S)-; mp 182° C. (dec).

EXAMPLE 34

1H-Imidazo[4,5-c]pyridine-6-carboxylic acid, 4,5,6,7-tetrahydro-1-(phenylmethyl)-5-[(3,4,5-trimethoxyphenyl)-acetyl]-, (S)-; mp 146°–146.5° C.

EXAMPLE 35

1H-Imidazo[4,5-c]pyridine-6-carboxylic acid, 5-[(3,4-dichlorophenyl)acetyl]-4,5,6,7-tetrahydro-1-(phenylmethyl)-, (S)-; mp 222°–226° C.

EXAMPLE 36

1H-Imidazo[4,5-c]pyridine-6-carboxylic acid, 4,5,6,7-tetrahydro-5-[(4-nitrophenyl)acetyl]-1-(phenylmethyl)-, (S)-; mp 270°–272° C.

EXAMPLE 37

1H-Imidazo[4,5-c]pyridine-6-carboxylic acid, 4,5,6,7-tetrahydro-5-[(4-hydroxy-3-nitrophenyl)acetyl]-1-phenylmethyl)-, (S)-; mp 243°–245° C.

EXAMPLE 38

1H-Imidazo[4,5-c]pyridine-6-carboxylic acid, 4,5,6,7-tetrahydro-1-(phenylmethyl)-5-[[(4-(trifluoromethyl)phenyl]acetyl]-, (S)-; mp 243°–245° C. (dec).

EXAMPLE 39

1H-Imidazo[4,5-c]pyridine-6-carboxylic acid, 5-[(4aminophenyl)acetyl]-4,5,6,7-tetrahydro-1-(phenylmethyl)-, dihydrochloride, (S)-; mp 260°–265° C.

EXAMPLE 40

1H-Imidazo[4,5-c]pyridine-5,6-carboxylic acid, 4,5,6,7-tetrahydro-1-(phenylmethyl)-, 5-phenylmethyl ester, (S)-; mp 208°–210° C. (dec).

EXAMPLE 41

1H-Imidazo[4,5-c]pyridine-6-carboxylic acid, 4,5,6,7-tetrahydro-5-(oxophenylacetyl)-1-(phenylmethyl)-, (S)-; MS (DEI) 389 (m).

EXAMPLE 42

1H-Imidazo[4,5-c]pyridine-6-carboxylic acid, 4,5,6,7-tetrahydro-5-[(2-methoxyphenyl)acetyl]-1-(phenylmethyl)-, (S)-; mp 122°–135° C.

EXAMPLE 43

1H-Imidazo[4,5-c]pyridine-6-carboxylic acid, 4,5,6,7-tetrahydro-5-[(2-hydroxyphenyl)acetyl]-1-(phenylmethyl)-, (S)-; mp 150°–166° C.

EXAMPLE 44

1H-Imidazo[4,5-c]pyridine-6-carboxylic acid, 4,5,6,7-tetrahydro-1-(phenylmethyl)-5-(3-pyridinylacetyl)-; mp 237°–238° C.

EXAMPLE 45

1H-Imidazo[4,5-c]pyridine-6-carboxylic acid, 5-(cyclohexylacetyl)-4,5,6,7-tetrahydro-1-(phenylmethyl)-, (S)-; mp 162°–175° C.

EXAMPLE 46

1H-Imidazo[4,5-c]pyridine-6-carboxylic acid, 4,5,6,7-tetrahydro-1-(phenylmethyl)-5-(9H-xanthen-9-ylcarbonyl)-; mp 256°–258° C.

EXAMPLE 47

1H-Imidazo[4,5-c]pyridine-6-carboxylic acid, 4,5,6,7-tetrahydro-5-(1H-indol-3-ylacetyl)-1-(phenylmethyl)-; mp 237°–240° C.

EXAMPLE 48

1H-Imidazo[4,5-c]pyridine-6-carboxylic acid, 4,5,6,7-tetrahydro-5-(1-naphthalenylacetyl)-1-(phenylmethyl)-, (S)-; MS (DEI) 425 (m).

EXAMPLE 49

1H-Imidazo[4,5-c]pyridine-6-carboxylic acid, 4,5,6,7-tetrahydro-5-(1-oxo-3,3-diphenylpropyl)-1-(phenylmethyl)-, (S)-; MS (DEI) 465 (m).

EXAMPLE 50

1H-Imidazo[4,5-c]pyridine-6-carboxylic acid, 4,5,6,7-tetra-5-(1H-inden-3-ylcarbonyl)-1-(phenylmethyl)-; mp 213°–215° C. (dec).

EXAMPLE 51

1H-Imidazo[4,5-c]pyridine-6-carboxylic acid, 5-[bis(-4methoxyphenyl)acetyl]-4,5,6,7-tetrahydro-1-(phenylmethyl)-, (S)-; NMR (DMSO-d6) 3.66 (s,3H,OMe); 3.69 (s,3H,OMe).

EXAMPLE 52

1H-Imidazo[4,5-c]pyridine-6-carboxylic acid, 5-[bis(-4methylphenyl)acetyl]-4,5,6,7-tetrahydro-1-(phenylmethyl)-, (S)-; NMR (DMSO-d ) 2.21 (s,3H,Me); 2.18 (s,3H,Me).

EXAMPLE 53

1H-Imidazo[4,5-c]pyridine-6-carboxylic acid, 4,5,6,7-tetrahydro-5-[[(4-methoxyphenyl)amino]carbonyl]-, (+)—; mp 225°–230° C.

EXAMPLE 54

1H-Imidazo[4,5-c]pyridine-6-carboxylic acid, 5-[bis(-4nitrophenyl)acetyl]-4,5,6,7tetrahydro-1-(phenylmethyl)-, (S)-; mp 154°–158° C.

EXAMPLE 55

1H-Imidazo[4,5-c]pyridine-6-carboxylic acid, 5-[bis(-4aminophenyl)acetyl]-4,5,6,7-tetrahydro-1-(phenylmethyl)-, (S)-; MS (FAB) 482 (m+1).

EXAMPLE 56

1H-Imidazo[4,5-c]pyridine-6-carboxylic acid, 4,5,6,7-tetrahydro-1-[(4-methoxy-3-methylphenyl)methyl]-5-(phenylacetyl)-, (S)-; mp 239°–240° C.

EXAMPLE 57

1H-Imidazo[4,5-c]pyridine-6-carboxylic acid, 5-[bis(4-fluorophenyl)acetyl]-4,5,6,7-tetrahydro-1-[(4-methoxy-3-methylphenyl)methyl]-, (S)-; NMR (DMSO-d6) 2.07 (s,3H,Me).

EXAMPLE 58

1H-Imidazo[4,5-c]pyridine-6-carboxylic acid, 4,5,6,7-tetrahydro-1-[(4-methoxy-3-methylphenyl)methyl]-S-(1-oxo-3-phenyl-3-propenyl)-, [S-(E)]-; mp 249°–257° C.

EXAMPLE 59

1H-Imidazo[4,5-c]pyridine-6-carboxylic acid, 4,5,6,7-tetrahydro-1-[(4-methoxy-3-methylphenyl)methyl]-5-[[(methoxyphenyl)amino]carbony1]-, (S)-; mp 175°–177° C.

EXAMPLE 60

1H-Imidazo[4,5-c]pyridine-6-carboxylic acid, 4,5,6,7-tetrahydro-1-[(4-methoxy-3-methylphenyl)methyl]-5-[(methylphenylamino)carbonyl]-, (S)-; MS (FAB) 435 (m+1).

EXAMPLE 61

1H-Imidazo[4,5-c]pyridine-6-carboxylic acid, 5-[bis(-4methoxyphenyl)acetyl]-4,5,6,7-tetrahydro-1-[(4-methoxy-3-methylphenyl)methyl]-, (S)-; NMR (DMSO-d6) 2.07 (s,3H,Me).

EXAMPLE 62

1H-Imidazo[4,5-c]pyridine-6-carboxylic acid, 4,5,6,7-tetrahydro-1-[(4-methoxy-3-methoxyphenyl)methyl]-5-(9H-xanthen-9-ylcarbonyl)-, (S)-; mp 255°–262° C.

EXAMPLE 63

1H-Imidazo[4,5-c]pyridine-6-carboxylic acid, 5-(9H-fluoren-9-ylcarbonyl)-4,5,6,7-tetrahydro-1-[(4-methoxy-3-methylphenyl)methyl]-, (S)-; mp 200°–205° C.

EXAMPLE 64

1H-Imidazo[4,5-c]pyridine-6-carboxylic acid, 4,5,6,7-tetrahydro-1-[(4-methoxy-3-methylphenyl)methyl]-5-(1-oxo-3,3-diphenylpropyl)-, (S)-; MS (FAB) 1019 (2m+1); 510 (m+1).

EXAMPLE 65

1H-Imidazo[4,5-c]pyridine-6-carboxylic acid, 4,5,6,7-tetrahydro-1-[(4-methoxy-3-methylphenyl)methyl]-5-(2-thienylacetyl)-, (S)-; mp 235°–237° C.

EXAMPLE 66

1H-Imidazo[4,5-c]pyridine-6-carboxylic acid, 4,5,6,7-tetrahydro-1-[(4-methoxy-3-methylphenyl)methyl]-5-(3-thienylacetyl)-, (S)-; mp 236°–238° C.

EXAMPLE 67

1H-Imidazo[4,5-c]pyridine-6-carboxylic acid, 4,5,6,7-tetrahydro-1-[(4-methoxy-3-methylphenyl)methyl]-5-(oxo-2-thienylacetyl)-, (S)-; mp 172°–180° C.

EXAMPLE 68

1H-Imidazo[4,5-c]pyridine-6-carboxylic acid, 5-[bis(4-nitrophenyl)acetyl]-4,5,6,7-tetrahydro-1-[(4-methoxy-3-methylphenyl)methyl]-, (S)-; mp 152°–158° C.

EXAMPLE 69

1H-Imidazo[4,5-c]pyridine-6-carboxylic acid, 5-[bis(4-chlorophenyl)acetyl]-4,5,6,7-tetrahydro-1-[(4-methoxy-3-methylphenyl)methyl]-, (S)-; mp 145°–154° C.

EXAMPLE 70

1H-Imidazo[4,5-c]pyridine-6-carboxylic acid, 5-(cyclohexylphenylacetyl)-4,5,6,7-tetrahydro-1-[(4-methoxy-3-methylphenyl)methyl]-; mp 140°–149° C.

EXAMPLE 71

1H-Imidazo[4,5-c]pyridine-6-carboxylic acid, 5-(diphenylacetyl)-4,5,6,7-tetrahydro-1-[(4-hydroxy-3-methylphenyl)-methyl]-, (S)-; mp 217°–225° C.

EXAMPLE 72

1H-Imidazo[4,5-c]pyridine-6-carboxylic acid, 5-(diphenylacetyl)-4,5,6,7-tetrahydro-1-[(3-methyl-4-nitrophenyl)-methy]-, (S)-; mp 158°–165° C.

EXAMPLE 73

1H-Imidazo[4,5-c]pyridine-6-carboxylic acid, 1-[(3,4-dimethylphenyl)methyl]-5-(diphenylacetyl)-4,5,6,7-tetrahydro-, (S)-; mp 238°–240° C.

EXAMPLE 74

1H-Imidazo[4,5-c]pyridine-6-carboxylic acid, 5-(diphenylacetyl)-4,5,6,7-tetrahydro-1-[(3-methylphenyl)methyl]-, methyl ester, monohydrochloride, (S)-; mp 130°–135° C.

EXAMPLE 75

1H-Imidazo[4,5-c]pyridine-6-carboxylic acid, 5-(diphenylacetyl)-4,5,6,7-tetrahydro-1-[(3-methylphenyl)methyl]-, (S)-; mp 134°–145° C.

EXAMPLE 76

1H-Imidazo[4,5-c]pyridine-6-carboxylic acid, 5-(diphenylacetyl)-4,5,6,7-tetrahydro-1-[(3-methyl-4-nitrophenyl)-methyl]-, methyl ester, (S)-; mp 168°–171° C.

EXAMPLE 77

1H-Imidazo[4,5-c]pyridine-6-carboxylic acid, 4,5,6,7-tetrahydro-1-[(4-hydroxyphenyl)methyl-]-6-(phenylacetyl)-, (S)-; mp 208°–212° C.

EXAMPLE 78

1H-Imidazo[4,5-c]pyridine-6-carboxylic acid, 5-(diphenylacetyl)-4,5,6,7-tetrahydro-1-[(4-methoxyphenyl)methyl]-, (S)-; mp 150°–160° C.

EXAMPLE 79

1H-Imidazo[4,5-c]pyridine-6-carboxylic acid, 4,5,6,7-tetrahydro-1-[(4-methoxyphenyl)methyl]-5-(phenylacetyl)-, (S)-; mp 228°–230° C.

EXAMPLE 80

1H-Imidazo[4,5-c]pyridine-6-carboxylic acid, 5-(diphenylacetyl)-4,5,6,7-tetrahydro-1-[(4-nitrophenyl)-methyl]-, (S)-; mp 210°–215° C.

EXAMPLE 81

1H-Imidazo[4,5-c]pyridine-6-carboxylic acid, 1-[(4-aminophenyl)methyl]-5-(diphenylacetyl)-4,5,6,7-tetrahydro-, (S)-; Lot P: mp 129°–131° C., Lot Q: mp 214°–216° C. (dec).

EXAMPLE 82

1H-Imidazo[4,5-c]pyridine-6-carboxylic acid, 1-[[(4(acetylamino)phenyl]methyl]-5-(diphenylacetyl)-4,5,6,7-tetrahydro-, (S)-; mp 254°–256° C.

EXAMPLE 83

1H-Imidazo[4,5-c]pyridine-6-carboxylic acid, 5-(diphenyl- acetyl)-4,5,6,7-tetrahydro-1-[2-methoxyphenyl)-methyl]-, (S)-; mp 148°–153° C.

EXAMPLE 84

1H-Imidazo[4,5-c]pyridine-6-carboxylic acid, 1-[[(4-(dimethylamino)phenyl]methyl]-5-(diphenylacetyl)-4,5,6,7-tetrahydro-; mp 166°–170° C.

EXAMPLE 85

1H-Imidazo[4,5-c]pyridine-6-carboxylic acid, 1-[[(4-(dimethylamino)phenyl]methyl]-5-(diphenylacetyl)-4,5,6,7-tetrahydro-, dihydrobromide; MS (DEI) 494 (m).

EXAMPLE 86

1H-Imidazo[4,5-c]pyridine-6-carboxylic acid, 1-[(3,4-dimethylphenyl)methyl]-5-(diphenylacetyl)-4,5,6,7-tetrahydro, (S)-; mp 238°–240° C.

EXAMPLE 87

1H-Imidazo[4,5-c]pyridine-6-carboxylic acid, 5-[bis-(4-fluorophenyl)acetyl]-4,5,6,7-tetrahydro-1-[(3-methyl-4-nitrophenyl)methyl], (S)-; mp 155°–165° C.

EXAMPLE 88

1H-Imidazo[4,5-c]pyridine-6-carboxylic acid, 1-[(4-amino-3-methylphenyl)methyl]-5-(cyclohexylphenylacetyl)-4,5,6,7-tetrahydro, (6S)-; mp 159°–164° C.

EXAMPLE 89

1H-Imidazo[4,5-c]pyridine-6-carboxylic acid, 1-[(4-amino-3-methylphenyl)methyl]-5-[bis(4-fluorophenyl)-acetyl]-4,5,6,7-tetrahydro-, (S)-; mp 198°–204° C.

EXAMPLE 90

1H-Imidazo[4,5-c]pyridine-6-carboxylic acid, 5-(diphenylacetyl)-1-[(4-fluorophenyl)methyl]-4,5,6,7-tetrahydro-; mp 158°–162° C.

EXAMPLE 91

1H-Imidazo[4,5-c]pyridine-6-carboxylic acid, 5-[(2,3-dihydro-1H-inden-1-yl)carbonyl]-4,5,6,7-tetrahydro-1-[(4-methoxy-3-methylphenyl)methyl]-, (6S)-; mp 247°–249° C.

EXAMPLE 92

1H-Imidazo[4,5-c]pyridine-6-carboxylic acid, 1-[[(4-(dimethylamino)phenyl]methyl-5-(diphenylacetyl)-4,5,6,7-tetrahydro-; NMR (CDCl$_3$) 1.14 (m,6H,2Me).

EXAMPLE 93

1H-Imidazo[4,5-c]pyridine-6-carboxylic acid, 4,5,6,7-tetrahydro-5-methyl-1-[(3-methyl-4-nitrophenyl)-methyl], methyl ester, (S)-; mp 103°–106° C.

EXAMPLE 94

1H-Imidazo[4,5-c]pyridine-6-carboxylic acid, 5-[bis-(4-fluorophenyl)acetyl]-1-[[4-(dimethylamino)-3-methyl-phenyl]methyl]-4,5,6,7-tetrahydro-, (S)-; mp 178°–182° C.

EXAMPLE 95

1H-Imidazo[4,5-c]pyridine-6-carboxylic acid, 1-[[(4-(acetylamino)-3-methylphenyl]methyl]-5-(diphenylacetyl)-4,5,6,7-tetrahydro-, (S)-; mp 175°–180° C.

EXAMPLE 96

1H-Imidazo[4,5-c]pyridine-6-carboxylic acid, 5-(diphenylacetyl)-4,5,6,7-tetrahydro-1-[[(3-methyl-4-[[(methylamino)carbonyl]amino]phenyl]methyl]-, (S)-; mp 198°–201° C.

EXAMPLE 97

1H-Imidazo[4,5-c]pyridine-6-carboxylic acid, 1-[[(4-(benzoylamino)-3-methylphenyl]methyl]-5-(diphenylacetyl)-, (S)-; mp 178°–185° C.

EXAMPLE 98

1H-Imidazo[4,5-c]pyridine-6-carboxylic acid, 5-[bis-(4-chlorophenyl)acetyl]-1-[[4-(dimethylamino)-3-methylphenyl]methyl]-4,5,6,7-tetrahydro-, (R)-; mp 243°–246° C. (dec).

EXAMPLE 99

1H-Imidazo[4,5-c]pyridine-6-carboxylic acid, 1-[[(4-(dimethylamino)-3-methylphenyl]methyl]-5-(diphenylacetyl)-4,5,6,7-tetrahydro-, (R)-; mp 255°–256° C. (dec).

EXAMPLE 100

1H-Imidazo[4,5-c]pyridine-6-carboxylic acid, 5-(diphenylacetyl)-4,5,6,7-tetrahydro-1-[(4-methoxy-3-nitrophenyl)methyl]-, (S)-; NMR (DMSO-d ) 3.93 (s,3H).

EXAMPLE 101

1H-Imidazo[4,5-c]pyridine-6-carboxylic acid, 5-(diphenylacetyl)-4,5,6,7-tetrahydro-1-[(4-methoxy-3-methyl-5-nitrophenyl)methyl]-, (S)-; mp 195°–199° C.

EXAMPLE 102

1H-Imidazo[4,5-c]pyridine-6-carboxylic acid, 4,5,6,7-tetrahydro-1-[(4-methoxy-3-methylphenyl)metehyl]-5-(1-oxo-2-phenylpropyl)-; mp 223° C. (dec).

EXAMPLE 103

1H-Imidazo[4,5-c]pyridine-6-carboxylic acid, 5-(diphenylacetyl)-1-[(3-ethyl-4-methoxyphenyl)methyl]-4,5,6,7-tetrahydro-; mp 137°–146° C.

EXAMPLE 104

1H-Imidazo[4,5-c]pyridine-6-carboxylic acid, 4,5,6,7-tetrahydro-1-[(4-methoxy-3-methylphenyl)methyl]-5-(tricyclo[3.3.1.1$^{3,7}$]dec-1-ylacetyl)-, (S)-; mp 210° C. (dec).

EXAMPLE 105

1H-Imidazo[4,5-c]pyridine-6-carboxylic acid, 4,5,6,7-tetrahydro-1-[(4-methoxy-3-methylphenyl)methyl]-5-(1-oxo-2,2-diphenylpropyl)-, (S)-; mp 210° C. (dec).

EXAMPLE 106

1H-Imidazo[4,5-c]pyridine-6-carboxylic acid, 4,5,6,7-tetrahydro-1-[(4-methoxy-3-methylphenyl)methyl]-5-[(1-phenylcyclohexyl)carbonyl]-, (S)-; mp 145° C. (dec).

EXAMPLE 107

1H-Imidazo[4,5-c]pyridine-6-carboxylic acid, 4,5,6,7-tetrahydro-1-[(4-methoxy-3-methylphenyl)methyl]-5-[(1-phenylcyclopentyl)carbonyl]-, (S)-; mp 195° C. (dec).

EXAMPLE 108

1H-Imidazo[4,5-c]pyridine-6-carboxylic acid, 5-[(4-chlorophenyl)phenylacetyl]-1-[[4-(dimethylamino)-3-methylphenyl]methyl]-4,5,6,7-tetrahydro-; mp 170°–190° C.

EXAMPLE 109

1H-Imidazo[4,5-c]pyridine-6-carboxylic acid, 5-[(2-chlorophenyl)(4-chlorophenyl)acetyl]-1-[[4-(dimethyl-amino)-3-methylphenyl]methyl]-4,5,6,7-tetrahydro-, (S)-; mp 175°–185° C.

EXAMPLE 110

1H-Imidazo[4,5-c]pyridine-6-carboxylic acid, 1-[(3,5-dibromo-4-methoxyphenyl)methyl]-5-(diphenylacetyl)-4,5,6,7-tetrahydro-, (S)-; mp 152°–157° C.

EXAMPLE 111

1H-Imidazo[4,5-c]pyridine-6-carboxylic acid, 5-[(4-chlorophenyl)(4-methylphenyl)acetyl]-1-[[4-(dimethylamino)-3-methylphenyl]methyl]-4,5,6,7-tetrahydro-; mp 170°–180° C.

EXAMPLE 112

1H-Imidazo[4,5-c]pyridine-6-carboxylic acid, 5-(diphenyl-acetyl)-4,5,6,7-tetrahydro-1-[[3-methyl-4[(3-methyl-1-oxobutyl)amino]phenyl]methyl]-, (S), methyl ester; MS (DEI) 578 (m).

EXAMPLE 113

1H-Imidazo[4,5-c]pyridine-6-carboxylic acid, 5-[(3-chlorophenyl)phenylacetyl]-1-[[4-(dimethylamino)3-methylphenyl]methyl]-4,5,6,7-tetrahydro-; mp 155°–165° C.

EXAMPLE 114

1H-Imidazo[4,5-c]pyridine-6-carboxylic acid, 5-(diphenylacetyl)-4,5,6,7-tetrahydro-1-[[3-methyl-4-[[[(1-methylethyl)amino]carbonyl]amino]phenyl]-methyl]-, (S)-; MS (FAB) 1131 (2m+1); 566 (m+1).

EXAMPLE 115

1H-Imidazo[4,5-c]pyridine-6-carboxylic acid, 5-(diphenylacetyl)-4,5,6,7-tetrahydro-1-[[3-methyl-4-[(3-methyl-1-oxobutyl)amino]phenyl]methyl]-, (S)-; MS (DEI) 564 (m).

EXAMPLE 116

1H-Imidazo[4,5-c]pyridine-6-carboxylic acid, 1-[(4-amino-3-methylphenyl)methyl]-5-[(3-chlorophenyl)-phenylacetyl]-4,5,6,7-tetrahydro-; mp 145°–160° C.

EXAMPLE 117

1H-Imidazo[4,5-c]pyridine-6-carboxylic acid, 1-[(4-amino-3-bromo-5-methylphenyl)methyl]-5-(diphenylacetyl)-4,5,6,7-tetrahydro-, (S)-; mp 225°–228° C.

EXAMPLE 118

1H-Imidazo[4,5-c]pyridine-6-carboxylic acid, 1-[(4-amino-3-methylphenyl)methyl]-5-[bis(4-chlorophenyl)-acetyl]-4,5,6,7-tetrahydro-, (S)-; mp 240°–250° C. (dec).

EXAMPLE 119

1H-Imidazo[4,5-c]pyridine-6-carboxylic acid, 5-[bis-(4-chlorophenyl)acetyl]-1-[[4-(dimethylamino)-3-methylphenyl]methyl]-4,5,6,7-tetrahydro-, (S)-; mp 160°–170° C.

EXAMPLE 120

1H-Imidazo[4,5-c]pyridine-6-carboxylic acid, 1-[(4-amino-3-bromo-5-methylphenyl)methyl]-5-(diphenylacetyl)-4,5,6,7-tetrahydro-, methyl ester; MS (DEI) 574 (m+1).

EXAMPLE 121

1H-Imidazo[4,5-c]pyridine-6-carboxylic acid, 1-[(4-amino-3-methylphenyl)methyl]-4,5,6,7tetrahydro-5-[(3-methylphenyl)phenylacetyl]-; mp 165°–175° C.

EXAMPLE 122

1H-Imidazo[4,5-c]pyridine-6-carboxylic acid, 1-[[(4-(dimethylamino)-3-methylphenyl]methyl]-4,5,6,7-tetrahydro-5-[(3-methylphenyl)phenylacetyl]-; mp 200°–210° C. (dec).

EXAMPLE 123

4,5,6,7-Tetrahydro-5-(2-phenylethyl)-1-(phenylmethyl)-1H-imidazo[4,5-c]pyridine-6-carboxylic acid, dihydrochloride.

Freshly dried molecular sieves (3 Å, 7.0 g) are added to a solution of 1-benzylspinacine dihydrochloride (3.4 g), 1.2 g phenylacetaldehyde and ethanol (50 mL). Triethylamine (2.0 g) is added and the mixture is stirred for 1 hr at room temperature. Bromocresol green (ca 0.10 mg) and sodium cyanoborohydride (1.3 g) are added. Ethanolic-hydrogen chloride is then added until color became light green over the course of 1 hr. After stirring two days at room temperature, ether (50 mL) is added and excess hydrogen chloride gas is passed in. When gas evolution ceases, the sieves and solids are filtered and the intermediate ester hydrochloride is precipitated with ether (300 mL) as a gum. The free base is prepared by treating a water (20 mL) solution of the hydrochloride with excess sodium bicarbonate and extraction into ethyl acetate; wt 1 2 g.

A solution of crude ester (1.1 g), methanol (20 mL) and 1N sodium hydroxide (10 mL) is heated at reflux for 10 min and concentrated to remove the methanol 1N Hydrochloric acid (10 mL) is added to precipitate the product as a gum. The aqueous portion is decanted and the remaining water is azeotroped by two successive additions and removed of absolute ethanol (50 mL). The remaining gum is dissolved in absolute ethanol (10 mL), filtered and treated with excess ethanolic hydrogen chloride (10 mL). Concentration gave the product which is recrystallized from ethanol-ether to give 0.10 g of the product as the dihydrochloride; mp 200°–205° C.

EXAMPLE 124

4,5,6,7-Tetrahydro-1,5-bis(phenylmethyl)-1H-imidazo[4,5-c]pyridine-6-carboxylic acid, methyl ester.

A solution of 2.0 g of 1-benzylspinacine, 20 mL of acetonitrile, 0.8 g of 1-methylamine and 1 3 g of benzyl bromide is allowed to stand at room temperature for four days. The solvent is removed, water (10 mL) is added and the product is extracted with ethyl acetate (10 mL) and ether (100 mL). Concentration gives the product which upon crystal-lization from ethyl acetate (8 mL) and petroleum ether gives a 5 pure sample; mp 91°–93° C.

EXAMPLE 125

4,5,6,7-Tetrahydro-5-[(methylphenylamino)carbonyl]-1-(phenylmethyl)-1H-imidazo[4,5-c]pyridine-6-carboxylic acid.

A solution of 1 0 g of the ester of Example 124, methanol (10 mL) and 1N sodium hydroxide (4.0 mL) is heated at reflux for 15 min. The methanol is removed and 2N hydrochloric acid (2.0 mL) is added to precipitate the product. Recrystallization from methanol gave a pure product; mp 220°–222° C.

The following Examples 126 through 134 illustrate preparation of selected compounds of formula II, using examples of Method A above for the preparation of intermediates:

EXAMPLE 126

1,4,6,7,8a,9-Hexahydro-7-phenyl-1-(phenylmethyl)-6-thioxo-8H-diimidazo[1,5-a:5'-d]pyridine-8-one.

Phenyl isothiocyanate (1.4 g) is added to a stirred mixture of 2.9 g of 1-benzylspinacine in dimethylformamide. The resulting solution is allowed to stand at room temperature for 15 min. Water (20 mL) is added to precipitate the product. Recrystallization from methanol gives 3.1 g; mp 224°–226° C.

EXAMPLE 127

6,7,8a,9-Tetrahydro-1-[(4-methoxy-3-methylphenyl)-methyl]-7-(4-methoxyphenyl)-6-thioxo-1H-diimidazo-[1,5-a:4',5'-d]-pyridine-8(4H)-one.

A solution of 1.7 g of 1-(4-methoxy-3-methyl)-benzylspinacine methyl ester, dimethylformamide (4 mL) and 4-methoxyphenylisothiocyanate (0.9 g) is heated on a steam bath for 15 min. Water (20 mL) is decanted and the residue is triturated with water. The resulting solid is filtered and washed with water. A crystalline hydrochloride salt was prepared as follows. The base was dissolved in warm (40°) 2-propanol (20 mL). Upon addition of concentrated hydrochloric acid (1.0 mL) product separated. Recrystallization from methanol-ether gave 1.40 g of pure product; mp 250°–265° C.

EXAMPLE 128

6,7,8a,9-Tetrahydro-7-(4-methoxyphenyl)-1-(phenylmethyl)-6-thioxo-1H-diimidazo[1,5-a:4',5'-d]pyridine-8(4H)-one.

A solution of 1.4 g of 1-benzylspinacine methyl ester, dimethylformamide (4 mL) and 4-methoxyphenylisothiocyanate (0.9 g) is heated on the steam bath for 15 min. Water (50 mL) is added to precipitate 2.5 g of a yellow solid. This is purified by precipitation from aqueous methanol to give 6,7,8a,9-tetrahydro-7-(4-methoxyphenyl)-1-(phenylmethyl)-6-thioxo- 1H-diimidazo[1,5-a:4',5'-d]pyridine-8(4H)-one; mp 100°–120° C.

EXAMPLE 129

(S)-8a,9-dihydro-3-methyl-7-(1-methylethyl)-3H-diimidazo-[1,5-a:4',5'-d]-pyridine-6,8(4H,7H)-dione.

Intermediate 3-methylspinacine dihydrochloride was prepared from 3-methyl-L-histidine (Vega Biochemical) by the method of Example 164 hereinafter.

A solution of 1-methylspinacine dihydrochloride (1.40 g) in 1N sodium hydroxide (16.5 mL, 0.0165 mole) and tetrahydrofuran (20 mL) is cooled to 5° C. Isopropylisocyanate (0.65 g) in tetrahydrofuran (5 mL) is added with stirring. After 1 hr at room temperature the THF is distilled and the aqueous solution is clarified. Concentrated hydrochloric acid (10 mL) is added. The solution is heated on the steam bath for 15 min and concentrated to dryness at reduced pressure. Water (5 mL) and solid potassium carbonate, to saturate, are added and the separated product is extracted into methylene chloride. Removal of solvent gives product. Recrystallization from ethyl acetate-petroleum ether gives the pure product, mp 161°–164° C.

EXAMPLE 130

8a,9-Dihydro-7-(1-methylethyl)-1-(phenylmethyl)- 1H-diimidazo[1,5-a:4',5'-d]pyridine-6,8(4H,7H)-dione hydrobromide.

This compound is prepared following the procedure of Example 129, however, the acid used in the cyclization step was hydrobromic acid, the product had mp 196°–198° C.

In a process analogous to the above Examples 126 through 129 and also as generally described in Method A above using appropriate starting materials the corresponding compounds of formula II are prepared 5 as follows:

EXAMPLE 131

3H-Diimidazo[1,5-a:4',5'-d]pyridine-6,8(4H,7H)-dione, 8a,9-dihydro-3-methyl-7-phenyl-; mp 199°–202° C.

EXAMPLE 132

1H-Diimidazo[1,5-a:4',5'-d]pyridine-6,8(4H,7H)-dione, 8a,9-dihydro-1-methyl-7-(1-methylethyl)-; mp 134°–137° C.

EXAMPLE 133

1H-Diimidazo[1,5-a:4',5'-d]pyridine-6,8(4H,7H)-dione, 8a,9-dihydro-7-(4-methoxyphenyl)-1-(phenylmethyl)-, monohydrochloride; mp 181°–187° C.

EXAMPLE 134

1H-Diimidazo[1,5-a:4',5'-d]pyridine-6,8(4H,7H)-dione, a,9-dihydro-1-[(4-methoxy-3-methylphenyl)methyl]-7-(4-methoxyphenyl)-, monohydrochloride, (S)-; mp 154°–159° C.

METHOD B

EXAMPLE 135

Methyl-5-diphenylacetyl-3-(2-oxo-2-phenylethyl)-4,5,6,7-tetrahydro-1H-imidazo[4,5-c]pyridine-6-carboxylate.

A suspension of 12.1 g histidine methyl ester dihydrochloride in 150 mL chloroform is treated at 0° C. with excess anhydrous ammonia. The resulting suspension is filtered and the filtrate is evaporated to give histidine methyl ester as an oil. This oil is dissolved in 100 mL dichloromethane and added dropwise to a refluxing solution of 8.1 g carbonyl diimidazole in 100 mL dichloromethane. Refluxing is continued 15 min after addition is complete then the reaction mixture is concentrated until it begins to crystallize. Ethyl ether is added and the solid is collected by filtration. Recrystallization from acetonitrile gives methyl-5,6,7,8-tetrahydro-5-oxoimidazo[1,5-c]-pyrimidine-7-carboxylate; mp 159°–164° C.

A mixture of 7.8 g of the above product, 8.0 g phenacyl bromide and 200 mL acetonitrile is heated at reflux 6 hr. The cooled suspension is filtered, rinsing with acetonitrile to afford 7-methoxycarbony12-(2-oxo-2-phenylethyl)-5,6,7,8-tetrahydro-5-oxo-imidazo-[1,5-c]pyrimidinium bromide; mp 223°–224° C. (decomposes with gas evolution).

The above imidazolium salt is treated with 250 mL 6N HCl at reflux for 4 hr and evaporated to a gum. This gum is dissolved in 500 mL ethanol, concentrated to a syrup and added dropwise to vigorously stirred ethyl acetate to give 3-(2-oxo-2-phenylethyl)histidine as a hygroscopic mixture of hydrochloride and hydrobromide salts. MS (FAB) 274 (M+1).

A solution of 33 g 3-(2-oxo-2-phenylethyl)histidine dihydrohalide in 400 mL 1N HCl is treated with 17.5 mL 36% formaldehyde, stirring 30 min at 25° C. followed by 2 hr at reflux. Evaporation gives a gum which crystallizes upon standing. Trituration with ethanol affords 3-(2-oxo-2-phenylethyl)-4,5,6,7-tetrahydro-3H-imidazo[4,5-c]pyridine-6-carboxylic acid as a mixture of hydrochloride and hydrobromide salts. MS (FAB) 286 (M+1).

The above carboxylic acid is converted to its methyl ester by dissolution in 400 mL methanol and treatment with 50 mL trimethyl orthoformate. The resulting solution is saturated with HCl and heated at reflux 6 hr. Upon cooling, the resulting slurry is concentrated to approximately 200 mL and filtered to give methyl-3-(2-oxo-2-phenylethyl)-4,5,6,7-tetrahydro-3H-imidazo[4,5-c]pyridine-6-carboxylate dihydrochloride as a white solid. MS (FAB) 300 (M+1).

A mixture of 9.3 g dicyclohexycarbodiimide, 6.1 g hydroxybenzotriazole hydrate, 9.5 g diphenylacetic acid and 100 mL acetonitrile is stirred at 25° C. for 15 min (suspension A). A mixture of 15.8 g methyl-3-(2-oxo-2-phenylethyl)-4,5,6,7-tetrahydro-3H-imidazo-[4,5-c]pyridine-6-carboxylate dihydrochloride, 14.8 mL diisopropylethylamine and 100 mL acetonitrile is stirred 10 min at 25° C. then treated with suspension A, using 100 mL acetonitrile to complete the transfer. The resulting suspension is stirred 48 hr, filtered and the filtrate is evaporated, dissolved in dichloromethane, washed with 10% Na$_2$CO$_3$, dried and evaporated. Chromatography on silica gel (chloroform-methanol, 99:1) gives methyl-5-diphenylacetyl-3-(2-oxo-2-phenyl-ethyl)-4,5,6,7-tetrahydro-1H-imidazo[4,5-c]pyridine-6-carboxylate as foam. MS (FAB) 494 (M+1).

EXAMPLE 136

Methyl-1-(3,4-dimethoxyphenyl)methyl-5-diphenylacetyl-4,5,6,7-tetrahydro-1H-imidazo[4,5-c]pyridine-6-carboxylate.

A solution of 1.5 g 3,4-dimethoxybenzyl chloride, 2.5 g methyl-5-diphenylacetyl-3-(2-oxo-2-phenylethyl)-4,5,6,7-tetrahydro-1H-imidazo[4,5-c]pyridine-6-carboxylate and 30 mL acetonitrile is heated at reflux 16 hr. The cooled solution is added dropwise to 400 mL vigorously stirred ether and the resulting precipitate is collected by filtration. This precipitate is dissolved in 40 mL methanol and treated with 8 g zinc dust and 40 mL acetic acid. The resulting suspension is sonicated 2 hr then the solution is filtered from excess zinc. The filtrate is dissolved in 400 mL dichloromethane and treated dropwise with 450 mL 10% Na$_2$CO$_3$ with vigorous stirring. The organic phase is separated, dried, concentrated and the major product is isolated by chromatography on silica gel (chloroform-methanol, 99:1) as a crisp foam. NMR (CDCl$_3$) 3.88 (s,3H,0Me); 3.80 (s,3H,0Me); 3.58 (s,3H,0Me).

EXAMPLE 137

1-(3,4-Dimethoxyphenyl)methyl-5-diphenylacetyl-4,5,6,7-tetrahydro-1H-imidazo[4,5-c]pyridine-6-carboxylic acid.

The methyl ester from Example 136 is saponified using the procedure described in Example 2 to give this acid as a white solid. MS (FAB) 512 (M+1).

EXAMPLE 138

Methyl-1-(3-trifluoromethylphenyl)methyl-5-diphenylacetyl-4,5,6,7-tetrahydro-1H-imidazo[4,5-c]pyridine-6-carboxylate.

A solution of 1.4 g 3-trifluoromethylbenzyl chloride, 3.0 g methyl-5-diphenylacetyl-3-(2-oxo-2-phenylethyl)-4,5,6,7-tetrahydro-1H-imidazo[4,5-c]pyridine-6-carboxylate and 20 mL acetonitrile is heated at reflux 16 hr. An additional 1 4 mL 3-trifluoromethylbenzyl chloride is added and refluxing continued 24 hr. The cooled solution is added dropwise to 400 mL vigorously stirred ether and the resulting precipitate is collected by filtration. This precipitate is dissolved in 60 mL methanol and treated with 10 g zinc dust and 60 mL acetic acid. The resulting suspension is sonicated 2 hr then th solution is filtered from excess zinc. The filtrate is dissolved in 400 mL dichloromethane and treated dropwise with 520 mL 10% $Na_2CO_3$ with vigorous stirring. The organic phase is separated, dried, concentrated and the major product is isolated by chromatography on silica gel (chloroform-methanol, 99.5:0.5) as a crisp foam. NMR ($CDCl_3$) 5.05 (s,2H,$NCH_2Ar$).

EXAMPLE 139

1-(3-Trifluoromethylphenyl)methyl-5-diphenylacetyl-4,5,6,7-tetrahydro-1H-imidazo[4,5-c]pyridine-6-carboxylic acid.

The methyl ester from Example 138 is saponified using the procedure described in Example 2 to give this acid as a white solid. MS (FAB) 520 (M+1); 1039 (2M+1).

EXAMPLE 140

Methyl-1-(3-methylphenyl)methyl-5-diphenylacetyl-4,5,6,7-tetrahydro-1H-imidazo[4,5-c]pyridine-6-carboxylate.

A solution of 2.7 mL 3-methylbenzyl bromide, 5.0 g methyl-5-diphenylacetyl-3-(2-oxo-2-phenyl-ethyl)-4,5,6,7-tetrahydro-1H-imidazo[4,5-c]pyridine-6-carboxylate and 50 mL acetonitrile is heated at reflux 4 hr. The cooled solution is added dropwise to 750 mL vigorously stirred ether and the resulting precipitate is collected by filtration. This precipitate is dissolved in 75 mL methanol and treated with 16 g zinc dust and 75 mL acetic acid. The resulting suspension is sonicated 6 hr then the solution is filtered from excess zinc. The filtrate is dissolved in 400 mL dichloromethane and treated dropwise with 650 mL 10% $Na_2CO_3$ with vigorous stirring. The organic phase is separated, dried, concentrated and the major product is isolated by chromatography on silica gel (chloroform-methanol, 99.5:0.5) as a crisp foam. NMR ($CDCl_3$) 4.97 (s,2H,$NCH_2Ar$).

EXAMPLE 141

1-(3-Methylphenylmethyl-5-diphenylacetyl-4,5,6,7-tetrahydro-1H-imidazo[4,5-c]pyridine-6-carboxylic acid.

The methyl ester from Example 140 is saponified using the procedure described in Example 2 to give this acid as a white solid. MS (DEI) 465 (M).

In a process analogous to the above Examples 135 through 141 and also as generally described in Method B above using appropriate starting materials the corresponding compounds of formula I are prepared as follows:

EXAMPLE 142

1H-Imidazo[4,5-c]pyridine-6-carboxylic acid, 5-(diphenylacetyl)-4,5,6,7-tetrahydro-1-(phenylmethyl)-, (S)-; mp 220°–225° C. (dec).

EXAMPLE 143

1H-Imidazo[4,5-c]pyridine-6-carboxylic acid, 5-(diphenylacetyl)-4,5,6,7-tetrahydro-1-[(3-methoxyphenyl)methyl]-, (S)-; mp 138°–150° C.

EXAMPLE 144

1H-Imidazo[4,5-c]pyridine-6-carboxylic acid, 5-(diphenylacetyl)-1-(diphenylmethyl)-4,5,6,7-tetrahydro-, (S)-; mp 157°–163° C.

EXAMPLE 145

1H-Imidazo[4,5-c]pyridine-6-carboxylic acid, 5-(diphenylacetyl)-4,5,6,7-tetrahydro-1-[(2-methoxy-5-methylphenyl)methyl]-, (S)-; mp 135°–154° C.

EXAMPLE 146

1H-Imidazo[4,5-c]pyridine-6-carboxylic acid, 1-[(3-bromophenyl)methyl]-5-(diphenylacetyl)-4,5,6,7-tetrahydro-, (S)-; mp 195°–215° C.

EXAMPLE 147

1H-Imidazo[4,5-c]pyridine-6-carboxylic acid, 1-[(3-chlorophenyl)methyl]-5-(diphenylacetyl)-4,5,6,7-tetrahydro-, (S)-; mp 137°–152° C.

EXAMPLE 148

1H-Imidazo[4,5-c]pyridine-6-carboxylic acid, 5-(diphenylacetyl)-4,5,6,7-tetrahydro-1-(2-naphthalenylmethyl)-, (S)-; mp 180° C. (dec)

EXAMPLE 149

1H-Imidazo[4,5-c]pyridine-6-carboxylic acid, 1-(3-bromo-4-methoxyphenyl)methyl-5-(diphenylacetyl)-4,5,6,7-tetrahydro-, (S)-; mp 150°–165° C.

METHOD C

EXAMPLE 150

(S)-4,5,6,7-tetrahydro-3H-imidazo[4,5-c]pyridine-6-carboxylic acid, methyl ester, dihydrochloride, 0.33 mole hydrate; (spinacine, methyl ester).

A mixture of 82 g of spinacine hydrochloride and methanol (2.5 L) is saturated with hydrogen chloride. The mixture is heated at reflux with stirring overnight. The resulting solution, at reflux, is again treated with a stream of hydrogen chloride for 1 hr and concentrated to half volume. Addition of ether (0.5 L) gives 92.60 g of product. Recrystallization from methanol-ether gives pure product containing 0.33 mole of water, mp 140°–160° C.; $[\alpha]_D^{23}$ −79.6° C. (1 08%, methanol).

EXAMPLE 151

(S)-8a,9-dihydro-7-phenyl-3H-diimidazo[1,5-a:4′,5′-d]pyridine-6,8-(4H,7H)-dione, 0.75 mole hydrate.

Phenylisocyanate (5.95 g) is added to a slurry of spinacine methyl ester dihydrochloride (12.7 g) dimethylformamide (150 mL) and triethylamine (15.2 g). After the mild exotherm (40° C.) the mixture is stirred at room temperature for 2 hr. The triethylamine hydrochloride is filtered and the filtrate is concentrated at reduced pressure. Water (200 mL) is added to the residue to give crude product. Recrystallization from methanol-water gives 9.8 g of II containing 0.75 mole water, mp 133°–136° C.; [α]$_D^{23}$ −201 3° C. (1 05%, methanol).

EXAMPLE 152

8a,9-Dihydro-7-phenyl-1-(phenylmethyl)-1H-diimidazo[1,5-a:4',5'-d]pyridine-6,8(4H,7H)-dione isomer A.

A solution of 27.3 g of the compound of Example 151 in 20% tetramethylammonium hydroxide-in-methanol (46.5 g) and dimethylformamide (60 mL) is treated with benzyl bromide (17.4 g). After ½ hr the separated solids are filtered, washed with dimethylformamide (50 mL) and then with water (200 mL) to give isomer A. Recrystallization from dimethylformamide gave 9.2 g of pure product, mp 277°–279° C.

Isomer B, 8a,9-dihydro-7-phenyl-3-(phenylmethyl)-1H-diimidazo-[1,5-a:4',5'-d]pyridine-6,8 (4H,7H)dione is isolated by precipitation with water from the above reaction filtrate. Purification of B is affected by trituration of the crude with acetone, filtration of solids, concentration of the acetone filtrate and recrystallization of the residue from dimethylformamide; mp 227°–229° C.

EXAMPLE 153

1-(Phenylmethyl)-4,5,6,7-tetrahydro-1H-imidazo[4,5-c]-pyridine-6-carboxylic acid, dihydrochloride; (also known as 1-benzyl-spinacine).

A solution of 9.0 g of the Isomer A compound of Example 152 in a solution of potassium hydroxide (18.0 g), water (13 mL) and methanol (40 mL) is maintained at reflux for 6 hr. The methanol is distilled at reduced pressure, water (15 mL) is added and the mixture is heated on the steam bath to dissolve clumps of solid. The cooled solution is extracted with ether (150 mL). Ice is added to the aqueous phase and concentrated hydrochloric acid (ca. 30 mL) is cautiously added to pH 2. This solution is passed through a cation exchange resin (ca. 200 g; Bio-Rad AGW50) and the column is washed with ca. three column volumes of water to remove inorganic salts. The product is removed from the column by passage of concentrated ammonium hydroxide (200 mL) and then water (250 mL). The ammonia fractions are concentrated at reduced pressure to give 6.0 g of the amorphous amino acid. The dihydrochloride salt is prepared as follows: a solution of 6.0 g of the above amino acid in water (5 mL) is treated with concentrated hydrochloric acid (5 mL). 2-Propanol (25 mL) is added and the mixture is filtered and washed with 2-propanol (10 mL) and ether to give product. Recrystallization from water gives a pure sample, mp 280°–282° C., dec.

EXAMPLE 154

8a,9-Dihydro-7-(1-methylethyl)-3H-diimidazo[1,5-a:4',5'-d]-pyridine-6,8(4H,7H)-dione.

This compound is prepared following the procedure of EXAMPLE 151 above using isopropyl isocyanate as the starting material. mp 149°–157° C.

EXAMPLE 155

8a,9-Dihydro-7-(4-methoxyphenyl)-1H-diimidazo[1,5-a:4',5'-d]pyridine-6,8(4H,7H)-dione.

This compound (mp 142°–140° C.) is prepared following the procedure of Example 151 above above using 4-methoxy-phenylisocyanate as the starting material. mp 142°–148° C.

EXAMPLE 156

7-(1,1-Dimethylethyl)-8a,9-dihydro-1H-diimidazo[1,5-a:4',5'-d]pyridine-6,8(4H,7H)-dione.

This compound is prepared following the procedure of Example 151 above using t-butyl isocyanate as starting material. The product has mp 156°–158° C.

EXAMPLE 157

7-(2,4-Dimethoxyphenyl)-8a,9-dihydro-1H-diimidazo[1,5-a:4',5'-d]pyridine-6,8(4H,7H)-dione.

This compound is prepared following the procedure of Example 151 above using 2,4-dimethoxyphenylisocyanate as starting material. The product has mp 241°–243° C. (dec).

EXAMPLE 158

8a,9-Dihydro-7-[4-(methylthio)pheny1-1H-diimidazo[1,5-a:4',5'-d]pyridine-6,8(4H,7H)-dione.

This compound is prepared by the procedure of Example 151 above using 4-(methylthio)phenylisocyanate as the starting material; the product has mp 241°–243° C. (dec).

EXAMPLE 159

1,4,6,7,8a,9-Hexahydro-7-(4-methoxyphenyl)-6-thioxo-8H-diimidazo[1,5-a:4',5'-d]pyridine-8-one.

A mixture of 10.0 g of spinacine hydrochloride, dioxane (250 mL) and triethylamine (5.00 g) is stirred at room temperature for 15 min. p-Methoxyphenylisothiocyanate (8.15 g) is added and the mixture is maintained at reflux under nitrogen for 24 hr. After filtration the solution is concentrated to give 18.77 g of product. Purification by silica gel chromatography gives 10.9 g of pure product, mp 266.5°–270° C. (dec)

EXAMPLE 160

7-[4-(Dimethylamino)phenyl]-1,4,6,7,8a,9-hexahydro-6-thioxo-8H-diimidazo[1,5-a:4',5'-d]pyridine-8-one.

This compound is prepared by the procedure of Example 159 above, using 4-(dimethylamino)phenylisothiocyanate as starting material. The product has mp 185°–200° C.

EXAMPLE 161

1,4,6,7,8a,9-Hexahydro-7-phenyl-6-thioxo-8H-diimidazo[1,5-a:4',5'-d]pyridine-8-one.

This compound is prepared following the procedure of Example 159 above and using phenylisothiocyanate as starting material. The product has mp 142°–143° C. (dec).

EXAMPLE 162

1,4,6,7,8a,9-Hexahydro-7-(1-methylethyl)-6-thioxo-8H-diimidazo-(1,5-a:4',5'-d]pyridine-8-one.

This compound is prepared following the procedure of Example 159 above using isopropylisothiocyanate as starting material. The product has mp 218°–220° C. (dec).

EXAMPLE 163

(S)-3-(phenylmethyl)-4,5,6,7-tetrahydro-1H-imidazo[4,5-c]pyridine-6-carboxylic acid, dihydrochloride, 1.5 moles hydrate; (3-benzylspinacine).

A solution of 24.5 g of im-benzylhistidine, concentrated hydrochloric acid (200 mL) and dimethoxymethane (60 mL) is allowed to stand at room temperature overnight. Additional dimethoxymethane (60 mL) is added and the solution is heated on a steam bath for 3 hr. Volatiles are removed at 55° C. and reduced pressure. The residue is dissolved in warm water (20 mL). 2-Propanol (250 mL) is added to precipitate the product. Recrystallization from water-2-propanol gives pure product, mp 130°–135° C.; $[\alpha]_D^{23}$ −72.8° C. (c=1.12%, methanol).

EXAMPLE 164

(S)-5-benzoyl-4,5,6,7-tetrahydro-3-(phenylmethyl)-3H-imidazo[4,5-c]pyridine-6-carboxylic acid.

A solution of 3-benzylspinacine, 2 HCl, 1.5 H$_2$O (1.79 g) in 1N sodium hydroxide (20 mL) and dioxane (30 mL) is cooled to 3° C. With stirring a solution of benzoyl chloride (0.70 g) in dioxane (3 mL) is added dropwise over 5 min. The ice bath is removed and, after 1 hr at room temperature, glacial acetic acid (ca. 0.5 g) is added to precipitate crude product. This is filtered and washed with water and ether to remove traces of benzoic acid. Recrystallization is accomplished by dissolution in methanol (5 mL), addition of water (20 mL) and removal of methanol by distillation to give pure product; mp 233°–235° C.; $[\alpha]_D^{23}$ −11.4° C. (1.12%, 0.1 N NaOH).

EXAMPLE 165

8a,9-Dihydro-7-(4-methoxyphenyl)-1-(phenylmethyl)-1H-diimidazo[1,5-a:4',5'-d]pyridine-6,8 (4H,7H)-dione, hydrochloride.

This compound is prepared following the procedure for Example 151 above using 4-methoxyphenylisocyanate as starting material. The product has mp 181°–187° C.

EXAMPLE 166

8a,9-Dihydro-1-[(4-methoxy-3-methylphenyl)methyl]7-(4-methoxyphenyl)-]H-diimidazo[1,5-a:4',5'-d]pyridine-6,8-(4H,7H)-dione.

This compound is prepared following the procedure of Example 151 above and using 1-(4-nitro-3-methyl)-benzylspinacine and 4-methoxyphenylisocyanate as starting materials. The product has mp 154°–159° C.; $[\alpha]_D^{23}$ = −104.9° C. (1 03, methanol).

EXAMPLE 167

4,5,6,7-Tetrahydro-1-[(4-methoxy-3-methylphenyl)methyl]5-[[(4-methoxyphenyl)amino]carbonyl]-1H-imidazo[4,5-c]pyridine-6-carboxylic acid.

A mixture of 7.5 g of 1-(4-methoxy-3-methyl)benzyl-spinacine hydrochloride, 1N-sodium hydroxide (60 mL) and tetrahydrofuran (20 mL) is cooled with stirring to 5° C. p-Methoxyphenylisocyanate (2.98 g) is added. After 10 min in the ice bath the mixture is stirred 1 hr at room temperature. The tetrahydrofuran is distilled at reduced pressure and solids are filtered. The clear filtrate is cooled in an ice bath and 1N hydrochloric acid (20 mL) is added to precipitate a solid. This is filtered, washed with water and added to methanol (50 mL) whereupon crystals separated. Filtration gave product. Recrystallization from methanol-methylene chloride gives pure product, mp 175°–177° C. dec; $[\alpha]_D^{23}$+40.0° C. (1.35% 50:50 methanol-chloroform).

EXAMPLE 168

5-(Diphenylacetyl)-4,5,6,7-tetrahydro-1-(phenylmethyl)-, 1H-imidazo[4,5-c]pyridine-6-carboxylic acid, methyl ester.

A solution of 2.0 g 1-benzylspinacine methyl ester in acetonitrile (25 mL) and 0.84 g triethylamine is cooled to 10° C. with stirring. A solution of 1 78 g diphenylacetyl chloride in acetonitrile (5 mL) is added slowly, keeping the temperature below 20° C. with cooling. After ½ hr at room temperature most of the acetonitrile is distilled at reduced pressure and ethyl acetate (50 mL), ether (50 mL) and ice water (50 mL) are added. The aqueous layer is separated and the organic layer is washed successively with water (50 mL) and 2% sodium bicarbonate solution (50 mL). The dried (MgSO$_4$) organic phase is charcoaled, filtered and concentrated to give 3.2 g of crude product. Crystallization from ethyl acetate-petroleum ether gives 1.6 g of the title compound, mp 127°–129° C.; NMR (CDCl$_3$) 3.49 (s,3H,OMe).

EXAMPLE 169

5-(Diphenylacetyl)-4,5,6,7-tetrahydro-1-(phenylmethyl)-1H-imidazo[4,5-c]pyridine-6-carboxylic acid A solution of 1 2 g of the methyl ester of 5 Example 168 above in methanol (10 mL) and 5.2 mL 1N sodium hydroxide is heated at reflux for 5 min. The methanol is distilled and water (30 mL) is added to the residue. The clear solution is treated with 1N hydrochloric acid to precipitate the product. Recrystallization from methanol-ether gives 0.8 g of a pure sample, mp 167°–169° C.

In a process analogous to the above Examples 151–169 and also as generally described in part by Method C above using appropriate starting materials the corresponding compounds of formula II are prepared as follows:

EXAMPLE 170

8H-Diimidazo[1,5-a:4',5'-d]pyridine-8-one, 1,4,6,7,8a,9-hexahydro-7-(4-nitrophenyl)-6-thioxo; mp 215°–216° C. (dec).

EXAMPLE 171

8H-Diimidazo[1,5-a:4',5'-d]pyridine-8-one, 1,4,6,7,8a,9-hexahydro-7-propyl-6-thioxo-; mp 85°–105° C.

EXAMPLE 172

8H-Diimidazo[1,5-a:4',5'-d]pyridine-8-one, 7-[4-ethoxyphenyl)-1,4,6,7,8a,9-hexahydro-6-thioxo-; mp 144°–145° C. (dec).

EXAMPLE 173

8H-Diimidazo[1,5-a:4',5'-d]pyridine-8-one, 7-ethyl-1,4,6,7,8a,9-hexahydro-6-thioxo-; NMR (CDCl$_3$) 1.23 (t,3H,Me).

EXAMPLE 174

1H-Diimidazo[1,5-a:4',5'-d]pyridine-6,8(4H.7H)-dione, 8a,9-dihydro-, monohydrochloride, (S)-; mp 315°–325° C.

EXAMPLE 175

3H-Diimidazo[1,5-a:4',5'-d]pyridine-6,8(4H,7H)-dione, 7-(2,6-dichlorophenyl)-8a,9-dihydro-, monohydrochloride (+)-; mp 345°–347° C.

EXAMPLE 176

1H-Diimidazo[1,5-a:4',5'-d]pyridine-6,8(4H,7H)-dione, 7-(4-chlorophenyl)-8a,9-dihydro-; MS (DEI) 303 (m+1).

EXAMPLE 177

1H-Diimidazo[1,5-a:4',5'-d]pyridine-6,8(4H,7H)-dione, -cyclohexyl-8a,9-dihydro-; MS (DEI) 274 (m).

EXAMPLE 178

1H-Diimidazo[1,5-a:4',5'-d]pyridine-6,8(4H,7H)-dione, 8a,9-dihydro-7-[3-(trifluoromethyl)phenyl]-; MS (DEI) 336 (m).

EXAMPLE 179

1H-Diimidazo[1,5-a:4',5'-d]pyridine-6,8(4H,7H)-dione, 8a,9-dihydro-7-(2-methoxyphenyl)-; mp 102°-104° C. (dec).

EXAMPLE 180

1H-Diimidazo[1,5-a:4',5'-d]pyridine-6,8(4H,7H)-dione, 8a,9-dihydro-7-(2-naphthalenyl)-; mp 158°-162° C.

EXAMPLE 181

1H-Diimidazo[1,5-a:4',5'-d]pyridine-6,8(4H,7H)-dione, 8a,9-dihydro-7-[4-(1-methylethyl)phenyl]-; mp 100°-106° C. (dec).

EXAMPLE 182

1H-Diimidazo[1,5-a:4',5'-d]pyridine-6,8(4H,7H)-dione, 8a,9-dihydro-7-[4-(methylsulfonyl)phenyl]-; mp 197°-207° C. (dec).

EXAMPLE 183

Benzoic acid, 4-(4,8,8a,9-tetrahydro-6,8-dioxo-1H-diimidazo[1,5-a:4',5'-d]pyridine-7(6H)-yl)-, ethyl ester; mp 115°-150° C.

EXAMPLE 184

1H-Diimidazo[1,5-a:4',5'-d]pyridine-6,8(4H,7H)-dione, 8a,9-dihydro-7-(4-phenoxyphenyl)-; mp 110°-130° C.

EXAMPLE 185

3H-Diimidazo[1,5-a:4',5'-d]pyridine-6,8(4H,7H)-dione, 8a,9-dihydro-7-(1-methylethyl)-, monohydrobromide; mp 273°-274° C.

EXAMPLE 186

1H-Diimidazo[1,5-a:4',5'-d]pyridine-6,8(4H,7H)-dione, 8a,9-dihydro-7-(3,4,5-trimethoxyphenyl)-; mp 157°-159° C.

EXAMPLE 187

1H-Diimidazo[1,5-a:4',5'-d]pyridine-6,8(4H,7H)-dione, 7-(2-chloro-6-methoxyphenyl)-8a,9-dihydro-; mp 250°-254° C. (dec).

EXAMPLE 188

1H-Diimidazo[1,5-a:4',5'-d]pyridine-6,8(4H,7H)-dione, 8a,9-dihydro-7-(3-methoxyphenyl)-; mp 157°-161.5° C.

EXAMPLE 189

1H-Diimidazo[1,5-a:4',5'-d]pyridine-6,8(4H,7H)-dione, 7-(3,5-dimethoxyphenyl)-8a,9-dihydro-; mp 237.5°-240° C. (dec).

EXAMPLE 190

3H-Diimidazo[1,5-a:4',5'-d]pyridine-6,8(4H,7H)-dione, 8a,9-dihydro-7-(phenylmethyl)-, monohydrochloride, (S)-; mp 260°-270° C.

EXAMPLE 191

1H-Diimidazo[1,5-a:4',5'-d]pyridine-6,8(4H,7H)-dione, 7-(3,4-dichlorophenyl)-8a,9-dihydro-; mp 135°-150° C. dec.

EXAMPLE 192

1H-Diimidazo[1,5-a:4',5'-d]pyridine-6,8(4H,7H)-dione, 8a,9-dihydro-7-(4-hydroxyphenyl)-; mp 271°-273° C. (dec).

EXAMPLE 193

1H-Imidazo[4,5-c]pyridine-6-carboxylic acid, 5-[(3,4-dichlorophenyl)acetyl]-4,5,6,7-tetrahydro-1-(phenylmethyl)-, (S)-; mp 222°-226° C.

EXAMPLE 194

1H-Diimidazo[1,5-a:4',5'-d]pyridine-6,8(4H,7H)-dione, 7-(2,6-dimethylpheyl)-8a,9-dihydro-; MS (DEI) 296 (m).

EXAMPLE 195

1H-Diimidazo[1,5-a:4',5'-d]pyridine-6,8(4H,7H)-dione, 7-(4-aminophenyl)-8a,9-dihydro-; mp 233°-243° C. (dec).

EXAMPLE 196

1H-Diimidazo[1,5-a:4',5'-d]pyridine-6,8(4H,7H)-dione, 7-(4-butoxyphenyl)-8a,9-dihydro-; mp 174°-175° C.

EXAMPLE 197

8H-Diimidazo[1,5-a 4',5'-d]pyridine-8-one, 7-(2-furanylmethyl)-1,4,6,7,8a,9-hexahydro-6-thioxo-, monohydro-bromide; mp 195° C. (dec).

EXAMPLE 198

1H-Diimidazo[1,5-a:4',5'-d]pyridine-6,8(4H,7H)-dione, 8a,9-dihydro-7-phenyl-1-(phenylmethyl)-, (±)-; mp 277°-279° C.

EXAMPLE 199

1H-Diimidazo[1,5-a:4',5'-d]pyridine-6,8(4H,7H)-dione, 8a,9-dihydro-7-phenyl-1-(2-propenyl)-; mp 204°-206° C.

EXAMPLE 200

1H-Diimidazo[1,5-a:4',5'-d]pyridine-6,8(4H,7H)-dione, 1-[(4-fluorophenyl)methyl]-8a,9-dihydro-7-phenyl-; mp 205°-206.5° C. (dec).

EXAMPLE 201

1H-Diimidazo[1,5-a:4',5'-d]pyridine-6,8(4H,7H)-dione, 8a,9-dihydro-1-[(4-methylphenyl)methyl]-7-phenyl-; mp 249°-253° C.

EXAMPLE 202

1H-Diimidazo[1,5-a:4',5'-d]pyridine-6,8(4H,7H)-dione, 8a,9-dihydro-7-phenyl-1-(3-phenylpropyl)-; mp 168°-169° C.

EXAMPLE 203

1H-Diimidazo[1,5-a:4',5'-d]pyridine-6,8(4H,7H)-dione, 8a,9-dihydro-7-[(4-methylthio)phenyl-1-(phenylmethyl)-; mp 202°-203° C.

EXAMPLE 204

1H-Diimidazo[1,5-a:4',5'-d]pyridine-6,8(4H,7H)-dione, 8a,9-dihydro-3-(phenylmethyl)-7-[3-(trifluoromethyl)phenyl]-; mp 171°-172.5° C.

EXAMPLE 205

1H-Diimidazo[1,5-a:4',5'-d]pyridine-6,8(4H,7H)-dione, 8a,9-dihydro-1-[(4-nitrophenyl)methyl]-7-phenyl-; mp 90° C.

EXAMPLE 206

1H-Diimidazo[1,5-a:4',5'-d]pyridine-6,8(4H,7H)-dione, 8a,9-dihydro-7-(2-naphthalenyl)-1-(phenylmethyl)-; mp 235°-238° C.

EXAMPLE 207

1H-Diimidazo[1,5-a:4',5'-d]pyridine-6,8(4H,7H)-dione, 8a,9-dihydro-7-[4-(1-methylethyl)phenyl]-1-(phenylmethyl)-; mp 220°-223° C. (dec).

EXAMPLE 208

3H-Diimidazo[1,5-a:4',5'-d]pyridine-6,8(4H,7H)-dione, 8a,9-dihydro-3-(phenylmethyl)-, (S)-; mp 230°-235° C.

EXAMPLE 209

3H-Diimidazo[1,5-a:4',5'-d]pyridine-6,8(4H,7H)-dione, 3-[(3-chlorophenyl)methyl]-8a,9-dihydro-7-phenyl-; mp 217°-225° C.

EXAMPLE 210

3H-Diimidazo[1,5-a:4',5'-d]pyridine-6,8(4H,7H)-dione, 8a,9-dihydro-3-[(4-nitrophenyl)methyl]-7-phenyl-; mp 240-244.

EXAMPLE 211

3H-Diimidazo[1,5-a:4',5'-d]pyridine-6,8(4H,7H)-dione, 3-[(4-fluorophenyl)methyl]-8a,9-dihydro-7-phenyl-; mp 242°-243° C. (dec).

EXAMPLE 212

3H-Diimidazo[1,5-a:4',5'-d]pyridine-6,8(4H,7H)-dione, 7-(4-chlorophenyl)-8a,9-dihydro-3-(phenylmethyl)-; mp 183°-184° C.

EXAMPLE 213

3H-Diimidazo[1,5-a:4',5'-d]pyridine-6,8(4H,7H)-dione, 8a,9-dihydro-3-[(4-methylphenyl)methyl]-7-phenyl-; mp 215°-219° C.

EXAMPLE 214

3H-Diimidazo[1,5-a:4',5'-d]pyridine-6,8(4H,7H)-dione, 8a,9-dihydro-3-[(3-methoxyphenyl)methyl]-7-phenyl-; mp 204°-205° C.

EXAMPLE 215

3H-Diimidazo[1,5-a:4',5'-d]pyridine-6,8(4H,7H)-dione, 8a,9-dihydro-7-[4-(methylthio)phenyl]-3-(phenylmethyl)-; mp 226°-228° C.

EXAMPLE 216

3H-Diimidazo[1,5-a:4',5'-d]pyridine-6,8(4H,7H)-dione, 8a,9-dihydro-7-phenyl-3-(3-phenylpropyl)-; mp 117°-118° C.

EXAMPLE 217

3H-Diimidazo[1,5-a:4',5'-d]pyridine-6,8(4H,7H)-dione, 7-cyclohexyl-8a,9-dihydro-3-(phenylmethyl)-; MS (DEI) 364 (m).

EXAMPLE 218

3H-Diimidazo[1,5-a:4',5'-d]pyridine-6,8(4H,7H)-dione, 8a,9-dihydro-7-[4-(methylsulfonyl)phenyl]-3-(phenylmethyl)-; mp 184°-190° C. (dec).

EXAMPLE 219

1H-Diimidazo[1,5-a:4',5'-d]pyridine-6,8(4H,7H)-dione, 8a,9-dihydro1-(phenylmethyl)-7-[3-(trifluoromethyl)-phenyl]-; mp 227°-230° C. (dec).

EXAMPLE 220

3H-Diimidazo[1,5-a:4',5'-d]pyridine-6,8(4H,7H)-dione, 8a,9-dihydro-7-(2-naphthalenyl)-3-(phenylmethyl)-; mp 232°-234° C.

EXAMPLE 221

3H-Diimidazo[1,5-a:4',5'-d]pyridine-6,8(4H,7H)-dione, 8a,9-dihydro-7-[4-(1-methylethyl)phenyl]-3-(phenylmethyl)-; mp 228°-229° C. (dec).

EXAMPLE 222

3H-Diimidazo[1,5-a:4',5'-d]pyridine-6,8(4H,7H)-dione, 8a,9-dihydro-7-(1-methylethyl)-3-(phenylmethyl)-, monohydrochloride; mp 246°-248° C.

EXAMPLE 223

1H-Imidazo[4,5-c]pyridine-6-carboxylic acid, 4,5,6,7-tetrahydro-5-[(phenylamino)carbonyl]-1-(phenylmethyl), (±)-; mp 270°-280° C.

EXAMPLE 224

1H-Imidazo[4,5-c]pyridine-6-carboxylic acid, 5-[[(4fluorophenyl)amino]carbonyl]-4,5,6,7-tetrahydro-1-(phenylmethyl)-; mp 209°-213° C.

EXAMPLE 225

1H-Imidazo[4,5-c]pyridine-6-carboxylic acid, 4,5,6,7-tetrahydro-5-[[(4-nitrophenyl)amino]carbonyl]-1-(phenyl-methyl)-; mp 192°-194° C. (dec)

EXAMPLE 226

1H-Imidazo[4,5-c]pyridine-6-carboxylic acid, 4,5,6,7-tetrahydro-5-[[(4-methylphenyl)amino]carbonyl]-1-(phenyl-methyl)-; mp 227°-235° C.

EXAMPLE 227

1H-Imidazo[4,5-c]pyridine-6-carboxylic acid, 5-[([(1,1'-biphenyl]-2-ylamino)carbonyl]-4,5,6,7-tetrahydro-1-(phenylmethyl)-; mp 158°-162° C. (dec).

EXAMPLE 228

1H-Imidazo[4,5-c]pyridine-6-carboxylic acid, 5-[[[4-(ethoxycarbonyl)phenyl]amino]carbonyl]-4,5,6,7-tetrahydro-1-(phenylmethyl)-; mp 173°-175° C. (dec).

EXAMPLE 229

1H-Imidazo[4,5-c]pyridine-6-carboxylic acid, 4,5,6,7-tetrahydro-1-[(4-methylphenyl)methyl]-5-[(phenylamino)carbonyl]-; NMR (DMSO-$d_6$) 2.27 (s,3H,Me).

EXAMPLE 230

1H-Imidazo[4,5-c]pyridine-6-carboxylic acid, 4,5,6,7-tetrahydro-5--[[[4-(methylthio)phenyl]amino]carbonyl]-1-(phenylmethyl)-; mp 201°-202° C.

EXAMPLE 231

1H-Imidazo[4,5-c]pyridine-6-carboxylic acid, 5-[[(4chlorophenyl)amino]carbonyl]-4,5,6,7-tetrahydro-1-(phenylmethyl)-; mp 203°-204° C. (dec).

EXAMPLE 232

1H-Imidazo[4,5-c]pyridine-6-carboxylic acid, 4,5,6,7-tetrahydro-5-[[[4-(methylsulfonyl)phenyl]amino]carbonyl]1-(phenylmethyl)-; mp 225°-226.5° C. (dec).

EXAMPLE 233

1H-Imidazo[4,5-c]pyridine-6-carboxylic acid, 4,5,6,7-tetrahydro-1-(phenylmethyl)-5-[[[3-(trifluoromethyl)phenyl]amino]carbonyl]-; mp 228°-231° C. (dec).

EXAMPLE 234

1H-Imidazo[4,5-c]pyridine-6-carboxylic acid, 4,5,6,7-tetrahydro-1-[(4-nitrophenyl)methyl]-5-[(phenylamino)carbonyl]-, monosodium salt; mp 160°-163° C. (dec).

EXAMPLE 235

1H-Imidazo[4,5-c]pyridine-6-carboxylic acid, 4,5,6,7-tetrahydro-5-[[(1-methylethyl)amino]carbonyl]-1-(phenyl-methyl)-; mp 170°-180° C. (dec).

EXAMPLE 236

3H-Imidazo[4,5-c]pyridine-6-carboxylic acid, 5-[[(1,1dimethylethyl)amino]carbonyl]-4,5,6,7-tetrahydro-3-(phenylmethyl)-, (S)-; mp 151°-154° C.

EXAMPLE 237

3H-Imidazo[4,5-c]pyridine-6-carboxylic acid, 4,5,6,7-tetrahydro-5-[(phenylamino)carbonyl]-3-(phenylmethyl)-; mp 222°-227° C. (dec).

EXAMPLE 238

3H-Imidazo[4,5-c]pyridine-6-carboxylic acid, 5-[[(2,6-dimethylphenyl)amino]carbonyl]-4,5,6,7-tetrahydro-3-(phenylmethyl)-, (S)-; mp 145°-150° C.

EXAMPLE 239

3H-Imidazo[4,5-c]pyridine-6-carboxylic acid, 4,5,6,7-tetrahydro-3-methyl-5-[(phenylamino)carbonyl]-; mp 176°-178° C. (dec).

EXAMPLE 240

3H-Imidazo[4,5-c]pyridine-6-carboxylic acid, 5-[[(4-chlorophenyl)amino]carbonyl]-4,5,6,7-tetrahydro-3-(phenylmethyl)-; mp 179°-182° C. (dec).

EXAMPLE 241

3H-Imidazo[4,5-c]pyridine-6-carboxylic acid, 4,5,6,7-tetrahydro-5-[[[4-(methylthio)phenyl]amino]carbonyl]-3-(phenylmethyl)-; mp 220°-224° C. (dec).

EXAMPLE 242

3H-Imidazo[4,5-c]pyridine-6-carboxylic acid, 5-[(cyclohexylamino)carbonyl]-4,5,6,7-tetrahydro-3-(phenylmethyl)-, monosodium salt; mp 182°-184.5° C. (dec).

EXAMPLE 243

3H-Imidazo[4,5-c]pyridine-6-carboxylic acid, 4,5,6,7-tetrahydro-5-[[[4-(methylsulfonyl)phenyl]amino]carbonyl]-3-(phenylmethyl)-; mp 180°-181° C. (dec).

EXAMPLE 244

3H-Imidazo[4,5-c]pyridine-6-carboxylic acid, 4,5,6,7-tetrahydro-3-[(4-nitrophenyl)methyl]-5-[(phenylamino)carbonyl]-; mp 240°-242° C. (dec).

EXAMPLE 245

3H-Imidazo[4,5-c]pyridine-6-carboxylic acid, 4,5,6,7-tetrahydro-5-[[(1-methylethyl)amino]carbonyl]-3-(phenylmethyl)-; mp 188°-190° C. (dec).

EXAMPLE 246

1H-Imidazo[4,5-c]pyridine-6-carboxylic acid, 5-benzoyl-4,5,6,7-tetrahydro-1-(phenylmethyl)-; mp 236°-238° C.

EXAMPLE 247

5H-Imidazo[4,5-c]pyridine-5,6-dicarboxylic acid, 1,4,6,7-tetrahydro-1-(phenylmethyl)-, 5-phenylmethyl ester; mp 123°-127° C.

EXAMPLE 248

1H-Imidazo[4,5-c]pyridine-6-carboxylic acid, 4,5,6,7-tetrahydro-5-(phenylacetyl)-1-(phenylmethyl)-; mp 221°-223° C.

EXAMPLE 249

1H-Imidazo[4,5-c]pyridine-6-carboxylic acid, 4,5,6,7-tetrahydro-5-[(methylphenylamino)carbonyl]-1-(phenylmethyl)-; mp 192°-195° C. (dec).

EXAMPLE 250

1H-Imidazo[4,5-c]pyridine-6-carboxylic acid, 4,5,6,7-tetrahydro-5-[(methylphenylamino)carbonyl]-1-(phenylmethyl)-, monohydrochloride; mp 204°-206° C. (dec).

EXAMPLE 251

1H-Imidazo[4,5-c]pyridine-6-carboxylic acid, 4,5,6,7-tetrahydro-5-(1-oxo-3-phenyl-2-propenyl)-1-(phenylmethyl)-; mp 242°-244° C.

EXAMPLE 252

1H-Imidazo[4,5-c]pyridine-6-carboxylic acid, 4,5,6,7-tetrahydro-1-(phenylmehhyl)-5-(phenoxyacetyl)-; mp 205°-208° C.

EXAMPLE 253

1H-Imidazo[4,5-c]pyridine-6-carboxylic acid, 5-acetyl-4,5,6,7-tetrahydro-1-(phenylmethyl)-; mp 225°-227° C.

EXAMPLE 254

1H-Imidazo[4,5-c]pyridine-6-carboxylic acid, 4,5,6,7-tetrahydro-5-[[methyl(2-phenylethyl)amino]carbonyl]1-(phenylmethyl)-; mp 134°–136° C.

EXAMPLE 255

1H-Imidazo[4,5-c]pyridine-6-carboxylic acid, 4,5,6,7-tetrahydro-5-[[methyl(phenylmethyl)amino]carbonyl]1-(phenylmethyl)-; mp 172°–174° C. (dec).

EXAMPLE 256

1H-Imidazo[4,5-c]pyridine-6-carboxylic acid, 4,5,6,7-tetrahydro-5-(1-oxo-3-phenylpropyl)-1-(phenylmethyl)-; mp 205°–207° C.

EXAMPLE 257

1H-Imidazo[4,5-c]pyridine-6-carboxylic acid, 5-[(ethylphenylamino)carbonyl]-4,5,6,7-tetrahydro-1-(phenylmethyl)-; mp 207°–209° C.

EXAMPLE 258

1H-Imidazo[4,5-c]pyridine-6-carboxylic acid, 4,5,6,7-tetrahydro-1-(phenylmethyl)-5-[(phenylmethyl)sulfonyl]-; mp 190°–192° C.

EXAMPLE 259

1H-Imidazo[4,5-c]pyridine-6-carboxylic acid, 4,5,6,7-tetrahydro-1-(phenylmethyl)-5-[(phenoxyacetyl)-; mp 205°–208° C.

EXAMPLE 260

1H-Imidazo[4,5-c]pyridine-6-carboxylic acid, 4,5,6,7-tetrahydro-1-(phenylmethyl)-5-[(phenylmethyl)sulfonyl]-, methyl ester, (S)-; mp 129°–131° C.

EXAMPLE 261

1H-Imidazo[4,5-c]pyridine-6-carboxylic acid, 4,5,6,7-tetrahydro-5-(2-methyl-1-oxo-3-phenyl-2-propenyl)-1-(phenylmethyl)-; mp 190°–192° C.

EXAMPLE 262

1H-Imidazo[4,5-c]pyridine-6-carboxylic acid, 4,5,6,7-tetrahydro-5-[(4-methylphenyl)sulfonyl]-1-(phenylmethyl)-, (±)-; mp 259°–261° C.

EXAMPLE 263

5H-Imidazo[4,5-c]pyridine-5-butanoic acid, 1,4,6,7-tetrahydro-6-(methoxycarbonyl)-γ-oxo-1-(phenylmethyl)-, methyl ester, (S)-; mp 125°–127° C.

EXAMPLE 264

1H-Imidazo[4,5-c]pyridine-6-carboxylic acid, 4,5,6,7-tetrahydro-5-(1-oxo-2,3-diphenyl-2-propenyl)-1-(phenylmethyl)-, [S-(E)]-; mp 225°–230° C.

EXAMPLE 265

3H-Imidazo[4,5-c]pyridine-6-carboxylic acid, 5-acetyl-4,5,6,7-tetrahydro-3-(phenylmethyl)-, methyl ester, (S)-; mp 155°–157° C.

EXAMPLE 266

3H-Imidazo[4,5-c]pyridine-6-carboxylic acid, 5-acetyl-4,5,6,7-tetrahydro-3-(phenylmethyl)-, (S)-; mp 120°–160° C.

EXAMPLE 267

5H-Imidazo[4,5-c]pyridine-5,6-dicarboxylic acid, 3,4,6,7-tetrahydro-3-(phenylmethyl)-, 5-phenyl ester; mp 174°–177° C. (dec).

EXAMPLE 268

3H-Imidazo[4,5-c]pyridine-6-carboxylic acid, 4,5,6,7-tetrahydro-5-(1-oxo-3-phenyl-2-propenyl)-3-(phenylmethyl)-, monohydrochloride; mp 254°–256° C.

Finally, Examples are hereinafter provided to illustrate processes to prepare the additional compounds of formula I and II.

EXAMPLE 269

2-Benzoyl-8a,9-dihydro-7-(1-methylethyl)--(phenylmethyl)-1H-diimidazo[1,5-a:4',5'-d]pyridine-6,8(4H,7H)-dione.

Trimethylamine (2.09 g) is added to a solution of 0.7 g of the compound of Example 55, dimethylformamide (50 mL) and benzoyl chloride (2.90 g). After 24 hr at room temperature water is added dropwise until turbidity develops. The separated crystals are filtered and washed with methanol (10 mL) and water to give a pale yellow solid. Recrystallization from methanol-methylene chloride gives 3.50 g of pure product; mp 215°–217° C.

EXAMPLE 270

3H-Diimidazo[1,5-a:4',5'-d]pyridine-6,8(4H,7H)-dione, 2-benzoyl-8a,9-dihydro-7-phenyl-; mp 213°–215° C.

EXAMPLE 271

3H-Diimidazo[1,5-a:4',5'-d]pyridine-6,8(4H,7H)-dione, 8a,9-dihydro-2-(4-nitrobenzoyl)-7-phenyl-3-(phenylmethyl)-; mp 230°–232° C.

EXAMPLE 272

3H-Diimidazo[1,5-a:4',5'-d]pyridine-6,8(4H,7H)-dione, 8a,9-dihydro-2-(4-methoxybenzoyl)-7-phenyl-3-(phenylmethyl)-; mp 200°–201° C.

EXAMPLE 273

1H-Diimidazo[1,5-c:4',5'-d]pyridine-6,8(4H,7H)-dione, 8a,9-dihydro-7-(4-methoxyphenyl)-1-[(3-methyl-4-nitrophenyl)methyl], monohydrochloride; mp 258°–261° C. (dec).

EXAMPLE 274

2-Benzoyl-4,5,6,7-tetrahydro-5-[[(1-methylethyl)amino]carbonyl]-1-(phenylmethyl)-1H-imidazo[4,5-c]pyridine-6-carboxylic acid.

A suspension of 0.5 g of the product from Example 269, methanol (50 mL) and 1N sodium hydroxide (10 mL) is heated on a steam bath for 15 min. The resulting solution is cooled in an ice bath and treated with 1N hydrochloric acid (10 mL) to precipitate the product. Filtration and trituration of the damp cake with methanol (2 mL) gives pure product; mp 192°–194° C. (dec).

EXAMPLE 275

3H-Imidazo[4,5-c]pyridine-6-carboxylic acid, 2-benzoyl-4,5,6,7-tetrahydro-5-[(phenylamino)carbonyl]-3-(phenylmethyl)-; mp 140°–145° C. (dec).

EXAMPLE 276

1H-Imidazo[4,5-c]pyridine-6-carboxylic acid, 2-benzoyl-4,5,6,7-tetrahydro-5-[(phenylamino)carbonyl]-1-(phenylmethyl)-; mp 180°–183° C. (dec).

EXAMPLE 277

3H-Imidazo[4,5-c]pyridine-6-carboxylic acid, 4,5,6,7-tetrahydro-2-(4-methoxybenzoyl)-5-[(phenylamino)-carbonyl]3-phenylmethyl)-; mp 172°–174° C. (dec).

EXAMPLE 278

(S)-1,4,6,7-tetrahydro-6-(t-butyldimethylsilyloxymethyl)-N-methyl-N-phenyl -1-(phenylmethyl)-5H-imidazo[4,5-c]-pyridine-5-carboxamide.

A mixture of 2.7 g of (S)-4,5,6,7-tetrahydro-1-(phenylmethyl)-1H-imidazo[4,5-c]pyridine-6-carboxylic acid methyl ester and 50 mL of tetrahydrofuran is stirred at 0° C. under a nitrogen atmosphere and 0.6 g at lithium aluminum hydride is slowly added. The ice bath is removed and the reaction mixture is allowed to stir for 15 hr. The mixture is quenched with 0.6 mL of water, 0.6 mL of a 15% sodium hydroxide solution and 1.7 mL of water and allowed to stir for 1 hr. The suspension is filtered and the filtrate is concentrated to give the amino alcohol as a light yellow solid, TLC (SiO$_2$) 10% MeOH/CHCl$_3$, R$_f$=0.15.

A mixture of 0.7 g of the above amino alcohol, 0.96 g of t-butyldimethylsilyl chloride, 0.49 g of imidazole and 15 mL of dry dimethylformamide is stirred at room temperature for 18 hr. The reaction mixture is concentrated, diluted with ethyl acetate and washed twice with water and twice with saturated sodium bicarbonate. The organic layer is dried over magnesium sulfate, filtered and concentrated. The residue is purified by flash chromatography on silica gel eluting with a 2.5% methanol and chloroform mixture. The desired fractions are combined and collected to afford the silyl ether as an oil; TLC (SiO$_2$) 10% MeOH/CHCl$_3$, R$_f$=0.55.

A mixture of 0.65 g of the above silyl ether 0.34 g of N-methyl, N-phenylcarbamoyl chloride, 0.56 mL of triethylamine and 10 mL dry tetrahydrofuran is stirred at room temperature for 24 hr. The reaction mixture is filtered and concentrated. The residue is flash chromatographed on silica gel eluting with a 2% methanol and chloroform mixture. The desired fractions are combined and concentrated to afford (S)-1,4,6,7-tetrahydro-6-(t-butyldimethylsilyloxymethyl)-N-methyl-N-phenyl-1-(phenylmethyl)-5H-imidazo[4,5-c]pyridine-5-carboxamide.

EXAMPLE 279

(S)-1,4,6,7-tetrahydro-6-(hydroxymethyl)-N-methyl-N-phenyl-1-(phenylmethyl)-5H-imidazo[4,5-c]pyridine-5-carboxamide.

A mixture of 3.80 g of (S) -1,4,6,7-tetrahydro-6-(t-butyldimethylsilyloxymethyl)-N-methyl-N-phenyl-1-(phenylmethyl)-5H-imidazo[4,5-c]pyridine-5-carboxamide and 100 mL of 2% hydrogen fluoride in acetonitrile (prepared by mixing 4 mL of a 48% aqueous hydrogen fluoride solution with 96 mL of acetonitrile) is stirred at room temperature for 1 hr. The solution is concentrated, diluted with ethyl acetate and washed with a saturated sodium bicarbonate solution. The organic layer is dried over magnesium sulfate, filtered and concentrated to dryness. The residue is purified by silica gel flash chromatography eluting with a 0°–2% methanol in chloroform progression. The desired fractions are concentrated to afford (S-1,4,6,7-tetrahydro-6-(hydroxymethyl)-N-methyl-N-phenyl-1-(phenylmethyl)-5H-imidazo[4,5-c]pyridine-5-carboxamide as a white solid, mp 65°–75° C.

EXAMPLE 280

(S) -5-(diphenylacetyl)-1,4,6,7-tetrahydro-1-[(4-methoxy-3-methylphenyl)methyl]-1H-imidazo[4,5-c]pyridine-6-methanol.

Following the procedure of Example 278 using (S)-4,5,6,7-tetrahydro-1-[(4-methoxy-3-methylphenyl)methyl]-1H-imidazo[4,5-c]pyridine-6-carboxylic acid methyl ester as the starting material in the first step and acylating with diphenylacetyl chloride in the third step and desilylating following the procedure of Example 279 afforded the desired product, mp 164°–170° C.

Using a process analogous to the above Examples 278 through 280 and using variations for the preparation of compounds of formula I above the following examples use appropriate corresponding starting materials for preparation of compound I as follows:

EXAMPLE 281

1H-Imidazo[4,5-c]pyridine-6-methanol, 4,5,6,7-tetrahydro-5-(phenylacetyl)-1-(phenylmethyl)-, (S)-; mp 119°–125° C.

EXAMPLE 282

1H-Imidazo[4,5-c]pyridine-6-methanol, 4,5,6,7-tetrahydro-5-(2-phenylethyl)-1-(phenylmethyl)-; tlc (SiO$_2$) R$_f$ 0.5 (1:4 MeOH/CHCl$_3$).

EXAMPLE 283

1H-Imidazo[4,5-c]pyridine-6-methanol, 5-[bis(4-chlorophenyl)acetyl]-4,5,6,7-tetrahydro-1-[(3-methyl-4-nitro-phenyl)methyl]-, (S)-; mp 178°–185° C.

EXAMPLE 284

1H-Imidazo[4,5-c]pyridine-6-methanol, 5-(diphenylacetyl)4,5,6,7-tetrahydro-1-[(3-methyl-4-nitrophenyl)methyl]-, (S)-; mp 187°–195° C.

EXAMPLE 285

1H-Imidazo[4,5-c]pyridine-6-methanol, 1-[[4-(dimethylamino)-3-methylphenyl]methyl]-5-(diphenylacetyl)-4,5,6,7-tetrahydro-, (S)-; mp 178°–185° C.

EXAMPLE 286

(S)-1,4,6,7-tetrahydro-2-bromo-6-(t-butyldimethylsilyloxymethyl)-N-methyl-N-phenyl-1-(phenylmethyl)-5H-imidazo[4,5-c]pyridine-5-carboxamide.

A mixture of 1.23 g of (S)-1,4,6,7-tetrahydro-6-(t-butyldimethylsilyloxymethyl)-N-methyl-N-phenyl-1-(phenylmethyl)-5H-imidazo[4,5-c]pyridine-5-carboxamide and 10 mL of methylene chloride is stirred at room temperature and 0.45 g of N-bromosuccinimide is added. The reaction mixture is stirred for 20 min and concentrated. The residue is purified by flash chromatography on silica gel eluting with a 50% ethyl acetate-hexane mixture. The desired fractions are combined and concentrated to afford the desired product as an oil; TLC (SiO$_2$) 50% EtOHc/hexane, R$_f$=0.35.

EXAMPLE 287

(S)-1,4,6,7-tetrahydro-2-butyl-6-(hydroxymethyl)-N-methyl-N-phenyl-1-(phenylmethyl)-5H-imidazo[4,5-c]-pyridine-5-carboxamide.

A mixture of 0.64 g of (S)-1,4,6,7-tetrahydro-2-bromo-6-(t-butyldimethylsilyloxymethyl)-N-methyl-N-phenyl-1-(phenylmethyl)-5H-imidazo[4,5-c]pyridine-5-carboxamide and 5 mL of tetrahydrofuran was cooled to −78° C. under a nitrogen atmosphere and 0.48 mL of a 2.35M solution of n-butyl lithium in hexane is added dropwise over a 5 min period. The solution is stirred for 15 min and a mixture of 0.14 g of n-butyl iodide in 1 mL of tetrahydrofuran is added dropwise over a 2 min period. After stirring at −78° C. for 30 min the dry ice-acetone bath is removed and the reaction mixture is allowed to warm to room temperature overnight. The solution is concentrated, diluted with ethyl acetate and washed with saturated sodium bicarbonate. The organic layer is dried over magnesium sulfate, filtered and concentrated. The residue is purified by flash chromatography eluting with a 1-4% methanol in chloroform progression and the desired fractions are combined and concentrated to afford the product as an oil; TLC (SiO$_2$) 5% MeOH/CHCl$_3$, R$_f$=0.5. Purification of the S isomer yielded a product having a mp of 70°-75° C.

EXAMPLE 288

(S)-1,4,6,7-tetrahydro-6-(t-butyldimethylsilyloxymethyl)-2-(hydroxyphenylmethyl)-1-(phenylmethyl-N-methyl-N-phenyl-5H-imidazo[4,5-c]pyridine-5-carboxamide.

Following the first step in the procedure outlined in Example 287 using the same starting material and benzeldehyde as the electrophile, the desired product can be prepared, TLC (SiO$_2$) 10% MeOH/CHCl$_3$, R$_f$=0.35.

EXAMPLE 289

(S)-1,4,6,7-tetrahydro-6-(hydroxymethyl)-N-methyl-N-phenyl-1,2-bis(phenylmethyl)-5H-imidazo[4,5-c]pyridine-5-carboxamide.

A mixture of 5.4 g of (S)-1,4,6,7-tetrahydro-6-(t-butyldimethylsilyloxymethyl)-2-(hydroxyphenylmethyl)-1-(phenylmethyl)-N-methyl-N-phenyl-5H-imidazo-[4,5-c]pyridine-5-carboxamide, 1.1 g of acetic anhydride, 1.33 g of dimethylaminopyridine, 1.4 g of diisopropylethylamine and 50 mL of methylene chloride is stirred at room temperature for 15 hr. The solution is concentrated, diluted with ethyl acetate and washed with successive portions of water, saturated copper sulfate, water and saturated sodium bicarbonate. The organic layer is dried over magnesium sulfate, filtered and concentrated to afford the acetate as an oil; TLC (SiO$_2$) 10% MeOH/CHCl$_3$, R$_f$=0.56.

The acetate (4.80 g) is desilylated using the procedure outlined in Example 279 to afford the alcohol, TLC (SiO$_2$) 10% MeOH/CHCl$_3$, R$_f$=0.35, mp 80°-87° C.

A mixture 1.5 g of the alcohol, 75 mL of methanol and 0.1 g of 20% palladium on charcoal catalyst is treated in a Parr pressure apparatus with hydrogen gas at an initial pressure of 50 psi at room temperature for 7 hr. The catalyst is removed by filtration and the filtrate is concentrated. The residue is purified by radial chromatography on a 4 mm silica gel plate eluting with a 0-3% methanol in chloroform progression. Concentration of the desired fractions affords the product as a white solid, mp 80°-87° C.

EXAMPLE 290

(S)-1,4,6,7-tetrahydro-6-(hydroxymethyl)-2-(hydroxyphenylmethyl)-1-(phenylmethyl)-N-methyl-N-phenyl-5H-imidazo[4,5-c]-pyridine-5-carboxamide.

Using (S)-1,4,6,7-tetrahydro-6-(t-butyldimethylsilyloxymethyl)-2-(hydroxyphenylmethyl)-1-(phenylmethyl)-N-methyl-N-phenyl-5H-imidazo[4,5-c]pyridine-5-carboxamide as the starting material and following the procedure outlined in Example 279 the product is obtained as a white solid, mp 107°-120° C.

EXAMPLE 291

5H-Imidazo[4,5-c]pyridine-5-carboxamide, 1,4,6,7-tetrahydro-6-(hydroxymethyl)-N,2-dimethyl-N-phenyl-1-(phenyl-methyl)-, (S)-; mp 130°-135° C.

EXAMPLE 292

5H-Imidazo[4,5-c]pyridine-5-carboxamide, 1,4,6,7-tetrahydro-2-[hydroxy-(4-methoxyphenyl)methyl]-6-hydroxymethyl)-N-methyl-N-phenyl-1-(phenylmethyl)-; mp 175°-180° C.

EXAMPLE 293

2-Bromo-8a,9-dihydro-7-phenyl-1-(phenylmethyl)-1H-diimidazo[1,5-a:4',5'-d]pyridine-6,8(4H,7H)-dione.

A solution of bromine (1.60 g) in methylene chloride is added slowly to a stirred mixture 3.6 g of the product from Example 152 in methylene chloride (150 mL). The resulting solution is stirred for ½ hr at room temperature, washed with water (150 mL), dried (MgSO$_4$) and concentrated to 20 mL. Addition of ethyl acetate (50 mL) resulted in precipitation of product. Recrystallization from dimethylformamideether gives pure compound, mp 267°-269° C.

EXAMPLE 294

1H-Imidazo[1,5-a:4',5'-d]pyridine-6-carboxylic acid, 2-bromo-4,5,6,7-tetrahydro-5-[(phenylamino)carbonyl]-1-(phenylmethyl)-; mp 270°-275° C.

EXAMPLE 295

3H-Diimidazo[1,5-a:4',5'-d]pyridine-6,8(4H,7H)-dione, 8a,9-dihydro-7-phenyl-2,3-bis(phenylmethyl)-; mp 181°-182° C.

EXAMPLE 296

3H-Imidazo[1,5-a:4',5'-d]pyridine-6-carboxylic acid, 4,5,6,7-tetrahydro-5-[(phenylamino)carbonyl]-2,3-bis-(phenylmethyl)-; mp 158°-160° C. (dec).

We claim:

1. A compound having the formula (I)

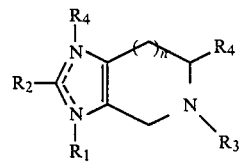

and their pharmaceutically acceptable base or acid addition salts; wherein (1) - - - is a single or a double bond;
(2) one of R$_1$ is present and is
   (a) alkyl of from four to twenty carbons, inclusive,
   (b)

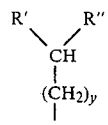

wherein y is zero, one, two, three, four or five, R' is cycloalkyl of from four to twenty carbons, inclusive in a one, two or three saturated ring system, said ring consisting of from four to eight carbons inclusive, each ring unsubstituted or substituted by a straight or branched lower alkyl group, naphthyl, heteroaryl consisting of 2-, 3-, or 4-pyridyl; 1-, 2-, or 4-imidazolyl; 1-, 2-, 3-, 4-, 5-, 6-, or 7-indolyl; 2-, or 3-thienyl; 2-, or 3-furyl; or 1-, 2-, or 3-pyrazolyl, phenyl unsubstituted or substituted with of from one through five substituents selected from the group consisting of lower alkyl, halo, trifluoromethyl, hydroxy, lower alkoxy, lower alkyl acyloxy, amino, N-lower monoalkylamino, N,N-lower dialkylamino, lower thioalkyl, lower alkylsulfonyl, nitro and

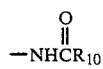

wherein $R_{10}$ is lower alkyl, phenyl unsubstituted or substituted by lower alkyl, or —NHR$_{11}$ wherein $R_{11}$ is hydrogen or lower alkyl, and R'' is hydrogen, lower alkyl, cycloalkyl of from four to twenty carbons, inclusive in a one two or three saturated ring system, said ring consisting of from four to eight carbons inclusive, each ring unsubstituted or substituted by a straight or branched lower alkyl group, naphthyl, phenyl unsubstituted or substituted with of from one through five substituents selected from the group consisting of alkyl, halo, trifluoromethyl, amino, N-lower monoalkylamino, N,N-lower dialkylamino, lower thioalkyl, lower alkylsulfonyl, and nitro;

(3) $R_2$ is
 (a) hydrogen,
 (b) halo,
 (c) lower alkyl,
 (d) R'—(CH$_2$)—$_x$ wherein x is one, two, three, four, or five and R' is independently as defined above,
 (e)

wherein R' is independently as defined above, or
 (f) R'—CH(OH)— wherein R' is independently as defined above;

(4) $R_3$ is
 (a) R'—(CH)$_{\overline{x}}$ wherein x and R' are independently as defined above,
 (b)

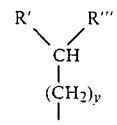

wherein R' and y are independently as defined above, and R''' is lower alkyl, cycloalkyl, of from four to twenty carbons, inclusive in a one, two or three saturated ring system, said ring consisting of from four to eight carbons inclusive, each ring unsubstituted or substituted by a straight or branched lower alkyl group, naphthyl, phenyl unsubstituted or substituted with of from one to five substituents selected from the group consisting of alkyl, halo, trifluoromethyl, amino, N-lower monoalkylamino, N,N-lower dialkylamino, lower thioalkyl, lower alkylsulfonyl, and nitro;

wherein $R_5$ is
(i) alkyl of from one to fifteen carbons, inclusive,
(ii)

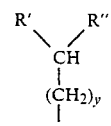

wherein R', R'', and y are independently as defined above,
(iv) —(CH=CR$_6$)—R$_1$ wherein R$_6$ is hydrogen or lower alkyl and R$_1$ is as defined above,
(v)

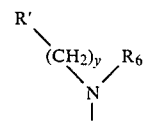

wherein y, R' and R$_6$ are independently as defined above,
(vi) R'—(CH$_2$)—$_y$—O— wherein y and R' are independently as defined above,
(vii)

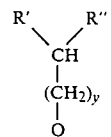

wherein R', R'', and y are independently as defined above,
(d)

wherein $R_5$ is independently as defined above;
(5) $R_4$ is
(a) —$CH_2OR_7$ wherein $R_7$ is hydrogen, lower acyl, a lower alkyl,
(b)

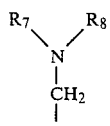

wherein $R_7$ is independently as defined above and $R_8$ is hydrogen, lower alkyl, or benzyl,
(c)

(d) —C≡N,
(e)

wherein $R_9$ is hydrogen, lower alkyl, or benzyl; and
(6) n is one; with the overall proviso that $R_9$ cannot be hydrogen, methyl or ethyl when $R_3$ is R'—(CH$_2$)—$_x$ or

wherein $R_5$ is R'—(CH$_2$)$_y$O— or

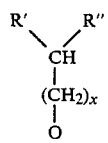

wherein each of R', R", x, and y are as defined above.

2. A compound of claim 1 wherein $R_2$ is H, n is one and $R_3$ is

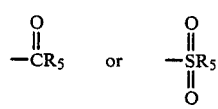

wherein $R_5$ is as defined above, $R_4$ is as defined above and $R_1$ is as defined above.

3. A compound of claim 2 wherein $R_3$ is

wherein $R_5$ is as defined above.

4. A pharmaceutical composition for treating hypertension in mammals comprising an antihypertensive effective amount of the compound of formula (I')

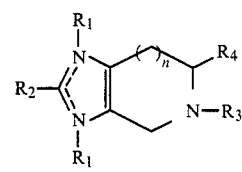

and their pharmaceutically acceptable base or acid addition salts; wherein
(1) - - - is a single or double bond;
(2) one of $R_1$ is present and is
(a) alkyl of from four to twenty carbons, inclusive
(b)

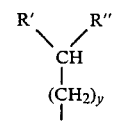

wherein y is zero, one, two, three, four or five, R' is cycloalkyl of from four to twenty carbons, inclusive in a one, two or three saturated ring system, said ring consisting of from four to eight carbons inclusive, each ring unsubstituted or substituted by a straight or branched lower alkyl group, naphthyl, heteroaryl consisting of 2-, 3-, or 4-pyridyl; 1-, 2-, or 4-imidazolyl; 1-, 2-, 3-, 4-, 5-, 6-, or 7-indolyl; 2-, or 3-thienyl; 2-, or 3-furyl; or 1-, 2-, or 3-pyrazolyl, phenyl unsubstituted or substituted with of from one through five substituents selected from the group consisting of lower alkyl, halo, trifluoromethyl, hydroxy, lower alkoxy, lower alkyl acyloxy, amino, N-lower monoalkylamino, N,N-lower dialkylamino, lower thioalkyl, lower alkylsulfonyl, nitro and

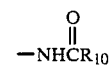

wherein $R_{10}$ is lower alkyl, phenyl unsubstituted or substituted by lower alkyl, or —NHR$_{11}$ wherein $R_{11}$ is hydrogen or lower alkyl, and R" is hydrogen, lower alkyl, cycloalkyl of from four to twenty carbons, inclusive in a one two or three saturated ring system, said ring consisting of from four to eight carbons inclusive, each ring unsubstituted or substituted by a straight or branched lower alkyl group, naphthyl, phenyl unsubstituted or substituted with of from one through five substituents selected from the group consisting of alkyl, halo, trifluoromethyl, amino, N-lower monalkylamino, N,N-lower dialkylamino, lower thioalkyl, lower alkylsulfonyl, and nitro;

(3) $R_2$ is
 (a) hydrogen,
 (b) halo,
 (c) lower alkyl,
 (d) $R'\text{-}(CH_2)_x\text{-}$ wherein x is one, two, three, four, or five and R' is independently as defined above,
 (e)

wherein R' is independently as defined above, or
 (f) R'—CH(OH)— wherein R' is independently as defined above;
(4) $R_3$ is
 (a) $R'\text{-}(CH_2)_x\text{-}$ wherein x and R' are independently as defined above,
 (b)

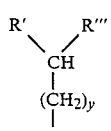

wherein R' and y are independently as defined above, and R''' is lower alkyl, cycloalkyl, of from four to twenty carbons, inclusive in a one, two or three saturated ring system, said ring consisting of from four to eight carbons inclusive, each ring unsubstituted or substituted by a straight or branched lower alkyl group, naphthyl, phenyl unsubstituted or substituted with of from one to five substituents selected from the group consisting of alkyl, halo, trifluoromethyl, amino, N-lower monoalkylamino, N,N-lower dialkylamino, lower thioalkyl, lower alkylsulfonyl, and nitro;
 (c)

wherein $R_5$ is
  (i) alkyl of from one to fifteen carbons, inclusive,
  (ii)

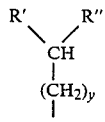

wherein R', R'', and y are independently as defined above,
  (iv) —(CH=CR$_6$)—R$_1$ wherein R$_6$ is hydrogen or lower alkyl and R$_1$ is as defined above,
  (v)

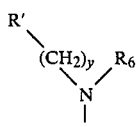

wherein y, R' and R$_6$ are independently as defined above,
  (vi) R'—(CH$_2$)$_y$—O— wherein y and R' are independently as defined above,
  (vii)

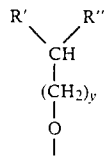

wherein R', R'', and y are independently as defined above,
 (d)

wherein R$_5$ is independently as defined above;
(5) $R_4$ is
 (a) —CH$_2$OR$_7$ wherein R$_7$ is hydrogen, lower acyl, a lower alkyl,
 (b)

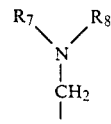

wherein R$_7$ is independently as defined above and R$_8$ is hydrogen, lower alkyl, or benzyl,
 (c)

(d) —C≡N,
 (e)

wherein R$_9'$ is hydrogen, lower alkyl, or benzyl; and
(6) n is one; together with a pharmaceutically acceptable carrier.

5. A method for treating hypertension in mammals suffering therefrom comprising administering to said mammals an antihypertensive effective amount of the composition according to claim 4.

6. A chemical compound according to claim 3 in which the compound is 1-(2-(1-adamantyl)ethyl)-5-diphenylacetyl-4,5,6,7-tetrahydro-1H-imidazo[4,5-c]pyridine-6-carboxylic acid.

7. A chemical compound according to claim 3 in which the compound is methyl-1-(4-amino-3-methylphenyl)methyl-5-diphenylacetyl-4,5,6,7-tetrahydro-1H-imidazo[4,5-c]pyridine-6-carboxylate.

8. A chemical compound according to claim 3 in which the compound is 1-(4-amino-3-methylphenyl)- methyl-5-diphenylacetyl-4,5,6,7-tetrahydro-1H-imidazo[4,5-c]pyridine-6-carboxylic acid.

9. A chemical compound according to claim 3 in which the compound is methyl-1-(4-dimethylamino-3-methylphenyl)methyl-5-diphenylacetyl-4,5,6,7-tetrahydro-1H-imidazo[4,5-c]pyridine-6-carboxylate.

10. A chemical compound according to claim 3 in which the compound 1-(4-dimethylamino-3-methylphenyl)methyl-5-dephenylacetyl-4,5,6,7-tetrahydro-1H-imidazo[4,5-c]pyridine-6-carboxylic acid.

11. A chemical compound according to claim 3 in which the compound is 1-(4-trifluoromethylphenyl)-methyl-5-diphenylacetyl-4,5,6,7-tetrahydro-1H-imidazo[4,5-c]pyridine-6-carboxylic acid.

12. A chemical compound according to claim 3 in which the compound is (S)-5-[bis(4-chlorophenyl)acetyl]-4,5,6,7-tetrahydro-1-(phenymethyl)-1H-imidazo[4,5,-c]pyridine-6-carboxylic acid.

13. A chemical compound according to claim 3 in which the compound is (S)-5-(cyclopentylphenylacetyl)-4,5,6,7-tetrahydro-1-[(4-methoxy-3-methylphenyl)methyl]-1H-imidazo [4,5-c]pyridine-6-carboxylic acid.

14. A chemical compound according to claim 3 in which the compound is 1H-imidazo[4,5-c]pyridine-6-carboxylic acid, 5-(diphenylacetyl)-4,5,6,7-tetrahydro-1-[(3-methylphenyl)methyl]-, (S)-.

15. A chemical compound according to claim 3 in which the compound is 5-(diphenylacetyl)-4,5,6,7-tetrahydro-1-(phenylmethyl)-1H-imidazo[4,5-c]pyridine-6-carboxylic acid.

16. A chemical compound according to claim 3 in which the compound is (S)-1,4,6,7-tetrahydro-6-(hydroxymethyl)-N-methyl-N-phenyl-1-(phenylmethyl)-5H-imidazo[4,5-c]pyridine-5-carboxamide.

* * * * *

UNITED STATES PATENT AND TRADEMARK OFFICE
CERTIFICATE OF CORRECTION

PATENT NO. : 4,812,462
DATED : March 14, 1989
INVENTOR(S) : Blankley, et al

It is certified that error appears in the above-indentified patent and that said Letters Patent is hereby corrected as shown below:

Column 58, lines 55-62, delete the structure

" 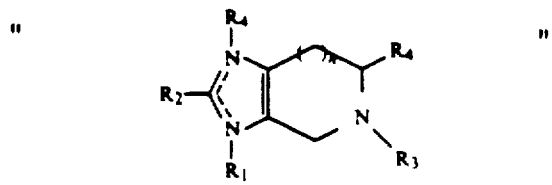 "

and insert instead

-- 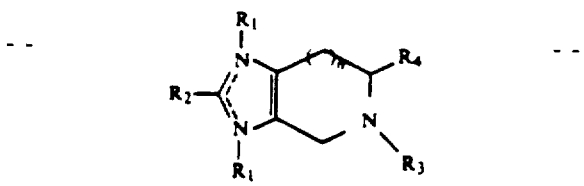 --

Signed and Sealed this

Eighth Day of February, 1994

Attest:

BRUCE LEHMAN

Attesting Officer          Commissioner of Patents and Trademarks